United States Patent
Miculka et al.

(10) Patent No.: US 7,153,955 B2
(45) Date of Patent: *Dec. 26, 2006

(54) PENTOPYRANOSYL NUCLEIC ACID ARRAYS, AND USES THEREOF

(75) Inventors: Christian Miculka, Frankfurt (DE); Norbert Windhab, Hattersheim (DE); Tilmann Brandstetter, München (DE); Gerhard Burdinski, Nastätten (DE)

(73) Assignee: Nanogen Recognomics GmbH, Frankfurt (DE)

( * ) Notice: Subject to any disclaimer, the term of this patent is extended or adjusted under 35 U.S.C. 154(b) by 573 days.

This patent is subject to a terminal disclaimer.

(21) Appl. No.: 10/150,402

(22) Filed: May 16, 2002

(65) Prior Publication Data

US 2003/0039997 A1 Feb. 27, 2003

Related U.S. Application Data

(63) Continuation of application No. 09/509,039, filed as application No. PCT/EP98/05999 on Sep. 21, 1998, now Pat. No. 6,506,896.

(30) Foreign Application Priority Data

Sep. 22, 1997 (DE) .............................. 197 41 715

(51) Int. Cl.
C07H 19/044 (2006.01)
C07H 21/04 (2006.01)
C12Q 1/68 (2006.01)
A61K 38/00 (2006.01)
C07K 16/00 (2006.01)

(52) U.S. Cl. ................... 536/26.9; 435/6; 435/7.1; 435/91.1; 536/23.1; 536/24.3; 530/300; 530/387.1

(58) Field of Classification Search ............... 536/26.9, 536/1.11, 23.1, 25.3, 26.71, 24.3, 27.1; 435/6, 435/88, 7.1, 91.1, 455, 91.5, 333, 91.3; 530/300, 530/324, 325, 387.1

See application file for complete search history.

(56) References Cited

U.S. PATENT DOCUMENTS

| | | | |
|---|---|---|---|
| 3,752,804 A | 8/1973 | Imai et al. | |
| 3,950,738 A | 4/1976 | Hayashi et al. | 365/185 |
| 3,995,190 A | 11/1976 | Salgo | 313/391 |
| 4,225,410 A | 9/1980 | Pace | 204/195 |
| 4,283,773 A | 8/1981 | Daughton et al. | 364/132 |
| 4,563,419 A | 1/1986 | Ranki et al. | 435/6 |
| 4,580,895 A | 4/1986 | Patel | 356/39 |
| 4,584,075 A | 4/1986 | Goldstein et al. | 204/522 |
| 4,594,135 A | 6/1986 | Goldstein | 204/551 |
| 4,661,451 A | 4/1987 | Hansen | 435/174 |
| 4,719,289 A | 1/1988 | Kolar et al. | |
| 4,751,177 A | 6/1988 | Stabinsky | 435/6 |
| 4,777,019 A | 10/1988 | Dandekar | |
| 4,787,963 A | 11/1988 | MacConnell | 204/450 |
| 4,807,161 A | 2/1989 | Comfort et al. | 364/550 |
| 4,816,418 A | 3/1989 | Mack et al. | 436/518 |
| 4,822,566 A | 4/1989 | Newman | 422/82 |
| 4,828,979 A | 5/1989 | Klevan et al. | 435/6 |
| 4,885,211 A | 12/1989 | Tang et al. | |
| 4,908,112 A | 3/1990 | Pace | 210/198 |
| 5,063,081 A | 11/1991 | Cozzette et al. | 435/4 |

(Continued)

FOREIGN PATENT DOCUMENTS

DE    35143168 A1    10/1986

(Continued)

OTHER PUBLICATIONS

Bolli, M. et al. "131. Pyranosyl-RNA: Further Observations on Replication" Helvetica Chimica Acta 80(6): 1901-51 (Sep. 22, 1997).

(Continued)

*Primary Examiner*—Jane Zara
(74) *Attorney, Agent, or Firm*—O'Melveny & Myers LLP

(57) ABSTRACT

The invention relates to a pentopyranosylnucleoside of the formula (I) or of the formula (II)

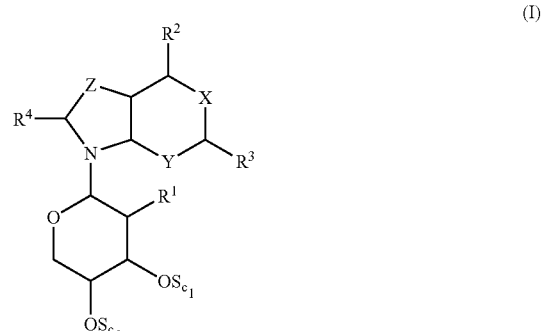

(I)

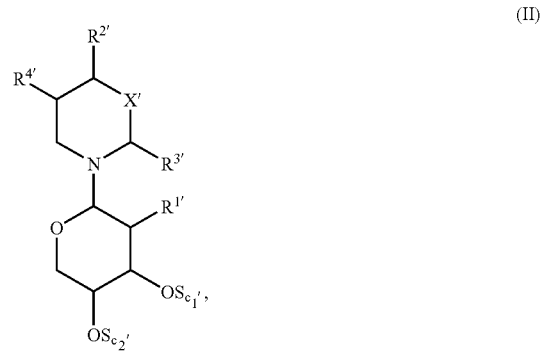

(II)

their preparation and use for the production of a therapeutic, diagnostic and/or electronic component.

3 Claims, 4 Drawing Sheets

U.S. PATENT DOCUMENTS

| | | | |
|---|---|---|---|
| 5,074,977 A | 12/1991 | Cheung et al. | 205/775 |
| 5,075,077 A | 12/1991 | Durley, III et al. | 422/56 |
| 5,087,952 A | 2/1992 | Ribi | |
| 5,096,669 A | 3/1992 | Lauks et al. | 422/61 |
| 5,096,807 A | 3/1992 | Leaback | 435/6 |
| 5,125,748 A | 6/1992 | Bjornson et al. | 356/414 |
| 5,126,022 A | 6/1992 | Soane et al. | 204/458 |
| 5,143,854 A | 9/1992 | Pirrung et al. | 436/518 |
| 5,164,319 A | 11/1992 | Hafeman et al. | 435/287 |
| 5,166,063 A | 11/1992 | Johnson | 435/173 |
| 5,200,051 A | 4/1993 | Cozzette et al. | 204/403 |
| 5,202,231 A | 4/1993 | Drmanac et al. | 435/6 |
| 5,219,726 A | 6/1993 | Evans | 435/6 |
| 5,227,265 A | 7/1993 | DeBoer et al. | 430/41 |
| 5,234,566 A | 8/1993 | Osman et al. | 204/403 |
| 5,242,797 A | 9/1993 | Hirschfeld | 435/6 |
| 5,304,487 A | 4/1994 | Wilding et al. | 435/29 |
| 5,312,527 A | 5/1994 | Mikkelsen et al. | 205/777 |
| 5,342,692 A | 8/1994 | Ribi | |
| 5,349,203 A | 9/1994 | Hanazato et al. | |
| 5,391,723 A | 2/1995 | Priest | |
| 5,433,819 A | 7/1995 | McMeen | 216/20 |
| 5,434,049 A | 7/1995 | Okano et al. | 435/6 |
| 5,436,129 A | 7/1995 | Stapleton | 435/6 |
| 5,445,525 A | 8/1995 | Broadbent et al. | 439/64 |
| 5,464,517 A | 11/1995 | Hjerten et al. | 204/183 |
| 5,468,646 A | 11/1995 | Mattingly et al. | 436/501 |
| 5,516,698 A | 5/1996 | Begg et al. | 436/89 |
| 5,527,670 A | 6/1996 | Stanley | 435/6 |
| 5,593,838 A | 1/1997 | Zanzucchi et al. | 435/6 |
| 5,605,662 A | 2/1997 | Heller et al. | 422/68 |
| 5,632,957 A | 5/1997 | Heller et al. | 422/68 |
| 5,653,939 A | 8/1997 | Hollis et al. | 422/50 |
| 5,660,701 A | 8/1997 | Grushka et al. | 204/451 |
| 5,681,751 A | 10/1997 | Begg et al. | 436/89 |
| 5,750,015 A | 5/1998 | Soane et al. | 204/454 |
| 5,789,167 A | 8/1998 | Konrad | 435/6 |
| 5,849,482 A | 12/1998 | Meyer et al. | |
| 5,849,486 A | 12/1998 | Heller et al. | 435/6 |
| 5,874,553 A | 2/1999 | Peyman et al. | |
| 6,013,166 A | 1/2000 | Heller | 204/469 |
| 6,017,696 A | 1/2000 | Heller et al. | 435/6 |
| 6,506,896 B1* | 1/2003 | Miculka et al. | 536/26.9 |
| 6,608,186 B1* | 8/2003 | Miculka et al. | 536/23.1 |
| 6,699,978 B1* | 3/2004 | Miculka et al. | 536/22.1 |

FOREIGN PATENT DOCUMENTS

| | | |
|---|---|---|
| EP | 0057548 | 8/1982 |
| EP | 0228075 | 7/1987 |
| EP | 0491059 A1 | 10/1996 |
| EP | 0739898 A2 | 10/1996 |
| GB | 2156074 | 10/1985 |
| GB | 2247889 | 3/1992 |
| GB | 2266182 A | 10/1993 |
| WO | WO86/03782 | 7/1986 |
| WO | WO88/08528 | 11/1988 |
| WO | WO89/01159 | 2/1989 |
| WO | WO89/10977 | 11/1989 |
| WO | WO90/01564 | 2/1990 |
| WO | WO92/04470 | 3/1992 |
| WO | WO93/22678 | 11/1993 |
| WO | WO 94/20589 A2 | 9/1994 |
| WO | WO95/07363 | 3/1995 |
| WO | WO 95/21184 A2 | 8/1995 |
| WO | WO96/01836 | 1/1996 |
| WO | WO 96/12728 A1 | 5/1996 |
| WO | WO 96/39414 A1 | 12/1996 |
| WO | WO 96/40711 A | 12/1996 |
| WO | WO 97/00882 A1 | 1/1997 |
| WO | WO 97/05156 A | 2/1997 |
| WO | WO 97/12896 A | 4/1997 |
| WO | WO 97/28176 A | 8/1997 |
| WO | WO98/01758 | 1/1998 |
| WO | WO98/51819 | 11/1998 |
| YU | 57087 | 8/1990 |

OTHER PUBLICATIONS

Doboszewski, B. et al. "Synthesis of 3'Deosy-3'-C-Hydromethyl-aldopentopyranosyl Nucleosides and their Incorporation into Oligonucleotides. Part II" Tetrahedron 51(45): 12319-12336 (1995).

Hayakawa, Y. et al. "O-Allyl Protection of Guanine and Thymine Residues in Oligodeoxyribonucleotides" J. Organic Chemistry 58: 5551-5555 (1993).

Nelson, P.S. "Oligonucleotide labeling methods 3" Nucleic Acids Research 20(23) 6253-59 (1992).

Niemeyer, B. Angew. Chem. 111/19, 3039 (1999).

Pitsch, Stefan et al. "147. Why Pentose- and Not Hexose Acids? Pyranosyl-RNA ('p-RNA')" Helvetica Chimica Acta 76(6): 2161-83 (1993).

Schlönvogt, I. et al. "188. Pyranosyl-RNA ('p-RN') NMR and Molecular Dynamics Study of the Duplex Formed by Self-Pairing of Ribopyranosyl-(C-G-A-A-T-T-C-G)." Helvetica Chimica Acta 79(8): 2316-45 (Dec. 1996).

Taktakishvili, M. et al. "Synthesis of 1-β-D-ribofuranosyl- and -ribofuranosyl-6-nitroindole and Indoline for Phosphotriester Oligonucleotide Synthesis" Chemical Abstracts 114(19), Abstract No. 185912 (May 13, 1991).

Taktakishvili, M. et al. "Synthesis of 1-β-D-ribofuranosyl- and -ribofuranosyl-6-nitroindole and Indoline for Phosphotriester Oligonucleotide Synthesis" Chemistry of Heterocyclic Compounds 26(11): 1249-54 (May 1991).

Tabone, J.C. et al. "Factors influencing the extent and regiospecificity of cross-link formation between single-stranded DNA and reactive complementary oligodeoxynuceotides" Biochemistry 33(1): 375-83 (1994).

Uddin, A.H. et al., "A novel N3-functionalized thymine linker for the stabilization of triple helical DNA" Chemical Communications 2: 171-2 (1996).

Adachi, Chihaya, et al. "Durability Characteristics of Aminopyrene Dimer Molecules as an Emitter in Organic Multilayered Eletroluminescent Diodes." Jpn. J. Appl. Phys. 35:4819-25 (1996).

Adams, David R. et al. "Preparation and Anti-HIV activity of N-3 Substituted Thymidine Nucleoside Analogs." J. Med. Chem. 40: 1550-58 (1997).

Cadet, J. "Chimie des Acides Nucleiques. Anomerisation et Isomerisation Furanno-Pyrannique des Derives Dihydro-5,6 Sulfonate-6 de lo Desoxy-2'-Uridine et de la Thymidine en Milieu Acide." Tetrahedron Letters 11: 867-70 (1974).

De Clercq, E., et al. "Ref. 132049y: Effects of E-5-(2-bromovinyl)-2'-deoxyuridine and other selective antiherpes compounds on the Induction of reterovirus particles in mouse BALB/373 cells." Chemical Abstracts 94: 36 (1981).

Doboszewski, B., et al. "3'-Deoxy-3'-Hydromethyl-aldopentopyranosyl Nucleoside Synthesis. Part I." Tetrahedron 51(18): 5381-96 (1995).

Edwards, Christine, et al. "Synthesis of 2-Substituted 2'-deoxyguanosines and 6-O-allylguanes via activation of C-2 by a trifluoromehtansulfonate group." J. Chem. Soc., Perkins Trans. 1:1887-93 (1997).

Gibson, Katharine J., et al. "Ref. 71626t: Synthesis and Application of derivatizable Oligonucleotides." Chemical Abstracts 108 (1988).

Gibson, Katharine J., et al. "Synthesis and application of derivatizable oligonucleotides." Nucleic Acids Research 15(16): 6455-67 (1987).

Gupta, Vineet et al. "A Self-Cleaving DNA Nucleoside." Chem. Commun. 1425-26 (1997).

Hanazato, Yoshio, et al. "Integrated Multi-Biosensors Based on an Ion-Sensitive Field-Effect Transistor Using Photolithographic Techniques." IEEE Transactions on Electron Devices 36(7): 1303-09 (1989).

Holy, A. "Preparation of Acyl Derivatives of Pyrimidin-2-one Nucleosides by the Silyl Variant of the Hilbert-Johnson Reaction." Collection Czechoslov. Chem. Commun. 42: 902-08 (1977).

Hossain, Nafizal, et al. "Synthesis and Antiviral Activity of the α-Analogues of 1,5-Anhydrohexitol Nucelotides (1,5-Anhydro-2,3-dideoxy-D-ribohexitol Nucleosides). " J. Org. Chem.. 62: 2442-47 (1997).

Iyer, Radhakrishnan P., et al. "N-pent-4-enoyl (PNT) Group as a Universal Nucleobase Protector: Applications in the Rapid and Facile Synthesis of Oligonucleotides, Analogs and Conjugates." Tetrahedron 53(8): 2731-50 (1997).

Kern, D.L., et al. "9-β-D-Ribopyranosylhypoxanthine, A Minor Component Produced by *Streptomyces Antibioticus.*" J. Heterocyclic Chem. 17: 461-63 (1980).

Lewis, A., et al. "Derivatives of the Nucleoside Antibiotics, Toyocamycin and Sangivamycin, Analogs of N6-(Δ$^2$-Isopentenyl)adenosine." J. Heterocyclic Chem. 11:71-72 (1974).

Nagatsugi, F., et al. "2-Aminopurine Derivatives with C6-Substituted Olefin as Novel Cross-linking Agents and the Synthesis of the Corresponding β-Phosphoramidite Precursors." Tetrahedron 53(9):3035-44 (1997).

Noda, Tetsuya, et al. "A novel yellow-emitting material, 5,5''-bis (4-methylphenyl) amino phenyl)-2-2':5'2 -tertiophene, for organic electroluminescent devices. Appl. Phys. Lett. 70(6): 699-701 (1997).

Pitsch, Stefan, et al. "Pyranosyl-RNA ('p-RNA'): Base Pairing Selectivity and Potential to Replicate." Helvetica Chemica Acta 78: 1621-35 (1995).

Taylor, M., et al. "Ribose-Modified Adensine Analogues as Adenosine Receptor Agonists." J. Med. Chem. 29: 346-53 (1986).

Torrence, Pail F., et al. "5-O-Alkylated Derivatives of 5-Hydroxy-2'-deoxyuridine as Potential Antiviral Agents: Anti-Herpes Activity of 5-Propynyloxy-2'-deoxyuridine." J. Med. Chem. 21(2): 228-31 (1978).

Watanabe, K.A., et al. "Nucelosides. LXXXVII. Total Synthesis of Pentopyranine A, an α-L Cytosine Nucleoside Elaborated by *Streptomyces griseochromogenes.*" J. Org. Chem. 39(17): 2482-86 (1974).

Xia, Xiaoyang, et al. "Stereo-controlled Synthesis of β-2'-deoxypyrimidine Nucelosides via Intrammolecular Glycosolations." Tetrahedron Letters 38(7): 1111-14 (1997).

Abrams et al. "Comprehensive Detection of Single Base Changes In Human Genomic DNA Using Denaturing Gradient Gel Electrophoresis & a GC Clamp". *Genomics*, 7, 1990, 463-475.

Anand and Southern "Pulsed Field Gel Electrophoresis," *Gel Electrophoresis of Nucleic Acids—A Practical Approach*, 2d. Ed., D. Rickwood and B.D. Hames (New York:IRL Press 1990), pp. 101-123.

Anderson and Young, "Quantitative Filter Hybridization," *Nucleic Acid Hybridization—A Practical Approach*, Eds. B.D. Hames and S.J. Higgins (Washington, D.C. :IRL Press 1985) pp. 73-111.

Bains, "Setting a Sequence to Sequence a Sequence," *Bio/Technology*, 10:757-758 (1992).

Baringa, "Will 'DNA Chip' Speed Genome Initiative?", *Science*, 253:1489 (1991).

Beattie et al., "Genosensor Technology," *The 1992 San Diego Conference: Genetic Recognition*, pp. 1-5 (Nov., 1992).

Beltz et al., "Isolation of Multigene Families and Determination of Homologies by Filter Hybridization Methods," *Methods in Enzymology*, 100:266-285 (1983).

Brown et al. "Electrochemically Induced Adsorption of Radio-Labelled DNA on Gold and HOPG Substrates for STM Investigations". *Ultramicroscopy*, 38, 1991, 253-264.

Conner et al., "Detection of Sickle Cell β$^3$-Globin Allele by Hybridization With Synthetic Oligonucleotides," *Proc. Natl. Acad. Sci. USA*, 80:278-282 (1983).

Drmanac et al., "Sequencing of Megabase Plus DNA by Hybridization: Theory of the Method," *Genomics*, 4:114-128 (1989).

Drmanac et al., "DNA Sequence Determination by Hybridization: A Strategy for Efficient Large-Scale Sequencing," *Science*, 260:1649-1652 (1993).

Eggers et al. "Biochip Technology Development", BioChip Technology Development Lincoln Laboratory Technical Report 901, Nov. 9, 1990.

Fiaccabrino et al., "Array of Individually Addressable Microelectrodes" *Sensors and Actuators B*, 18-19 (1994) 675-677.

Fodor et al., "Multiplexed Biochemical Assays With Biological Chips," *Nature*, 364:555-556 (1993).

Fodor et al., "Light-Directed, Spatially Addressable Parallel Chemical Synthesis," *Science*, 251:767-773 (1992).

Horejsi, "Some Theoretical Aspects of Affinity Electrophoresis," *Journal of Chromatography*, 178:1-13 (1979).

Horejsi et al., Determination of Dissociation Constants of Lectin Sugar Complexes by Means of Affinity Electrophoresis, *Biochimica at Biophysica Acta*, 499:200-300 (1977).

Kakerow et al., "A Monolithic Sensor Array of Individually Addressable Microelectrodes", *Sensors and Actuators A*, 43 (1994) 296-301.

Mathews, Kricka. "Analytical Strategies For The Use Of DNA Probes". *Analytical Biochemistry*, 169, 1988, 1-25.

Palecek. "New Trends in Electrochemical Analysis of Nucleic Acids". *Bioelectrochemistry and Bioenergetics*, 20, 1988, 179-194.

Ranki et al., "Sandwich Hybridization as a Convenient Method for the Detection of Nucleic Acids in Crude Samples," *Gene*, 21:77-85 (1983).

Saiki, "Amplication of Genomic DNA," *PCR Protocols: A Guide to Methods and Applications*, (Academic Press, Inc. 1990), pp. 13-20.

Southern et al., "Analyzing and Comparing Nucleic Acid Sequences by Hybridization to Arrays of Oligonucleotides Evaluation Using Experimental Models," *Genomics*, 13:1008-1017 (1992).

Strezoska et al., "DNA Sequencing by Hybridization: 100 Bases Read by a Non-Gel-Based Method", *Proc. Natl. Acad. Sci. USA*, 88:11089-93 (1991).

Wallace et al., "Hybridization of Synthetic Oligodexribonucleotides to Φx174 DNA: The Effect of Single Base Pair Mismatch," *Nucleic Acid Res.*, 6:3543-3557 (1979).

Washizu, "Electrostatic Manipulation of Biological Objects," *Journal of Electrostatics*, 25:109-123 (1990).

Washizu and Kurosawa, "Electrostatic Manipulation of DNA in Microfabricated Structures," *IEEE Transactions on Industry Applications*, 26:1165-1172 (1990).

\* cited by examiner

PENTOPYRANOSYL NUCLEIC ACID ARRAYS, AND USES THEREOF

This is a continuation of U.S. application Ser. No. 09/509,039 filed Jul. 11, 2000, now U.S. Pat. No. 6,506,896 which in turn is a national stage application of international application PCT/EP98/05999, filed Sep. 21, 1998, which in turn claims priority to German Application No. 197 41 715.9, filed Sep. 22, 1997. All of the above applications are expressly incorporated herein by reference.

The present invention relates to a pentopyranosylnucleoside of the formula (I) or of the formula (II)

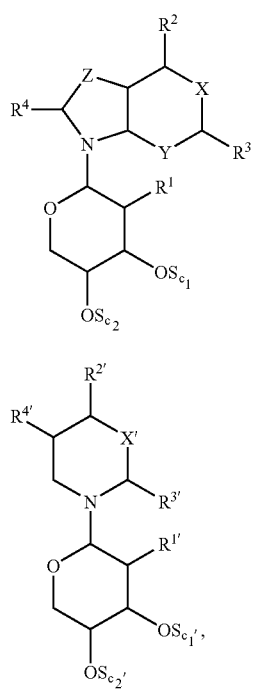

its preparation and use for the production of an electronic component, in particular in the form of a diagnostic.

Pyranosylnucleic acids (p-NAs) are in general structural types which are isomeric to the natural RNA, in which the pentose units are present in the pyranose form and are repetitively linked by phosphodiester groups between the positions C-2' and C-4' (FIG. 1). "Nucleobase" is understood here as meaning the canonical nucleobases A, T, U, C, G, but also the pairs isoguanine/isocytosine and 2,6-diaminopurine/xanthine and, within the meaning of the present invention, also other purines and pyrimidines. p-NAs, namely the p-RNAs derived from ribose, were described for the first time by Eschenmoser et al. (see Pitsch, S. et al. Helv. Chim. Acta 1993, 76, 2161; Pitsch, S. et al. Helv. Chim Acta 1995, 78, 1621; Angew. Chem. 1996, 108, 1619–1623). They exclusively form so-called Watson-Crick-paired, i.e. purine-pyrimidine- and purine-purine-paired, antiparallel, reversibly "melting", quasilinear and stable duplexes. Homochiral p-RNA strands of the opposite sense of chirality likewise pair controllably and are strictly non-helical in the duplex formed. This specificity, which is valuable for the construction of supramolecular units, is associated with the relatively low flexibility of the ribopyranose phosphate backbone and with the strong inclination of the base plane to the strand axis and the tendency resulting from this for intercatenary base stacking in the resulting duplex and can finally be attributed to the participation of a 2',4'-cis-disubstituted ribopyranose ring in the construction of the backbone. These significantly better pairing properties make p-NAs pairing systems to be preferred compared with DNA and RNA for use in the construction of supramolecular units. They form a pairing system which is orthogonal to natural nucleic acids, i.e. they do not pair with the DNAs and RNAs occurring in the natural form, which is of importance, in particular, in the diagnostic field.

Eschenmoser et al. (1993, supra) has for the first time prepared a p-RNA, as shown in FIG. 2 and illustrated below.

In this context, a suitable protected nucleobase was reacted with the anomer mixture of the tetrabenzoylribopyranose by action of bis(trimethylsilyl)acetamide and of a Lewis acid such as, for example, trimethylsilyl trifluoromethanesulphonate (analogously to H. Vorbrüggen, K. Krolikiewicz, B. Bennua, Chem. Ber. 1981, 114, 1234). Under the action of base (NaOH in THF/methanol/water in the case of the purines; saturated ammonia in MeOH in the case of the pyrimidines), the acyl protected groups were removed from the sugar, and the product was protected in the 3',4'-position under acidic catalysis with p-anisaldehyde dimethyl acetal. The diastereomer mixture was acylated in the 2'-position, and the 3',4'-methoxybenzylidene-protected 2'-benzoate was deacetalized by acidic treatment, e.g. with trifluoroacetic acid in methanol, and reacted with dimethoxytrityl chloride. The 2'→3' migration of the benzoate was initiated by treatment with p-nitrophenol/4-(dimethylamino) pyridine/triethylamine/pyridine/n-propanol. Almost all reactions were worked up by column chromatography. The key unit synthesized in this way, the 4'-DMT-3'-benzoyl-1'-nucleobase derivative of the ribopyranose, was then partly phosphitylated and bonded to a solid phase via a linker.

In the following automated oligonucleotide synthesis, the carrier-bonded component in the 4'-position was repeatedly acidically deprotected, a phosphoramidite was coupled on under the action of a coupling reagent, e.g. a tetrazole derivative, still free 4'-oxygen atoms were acetylated and the phosphorus atom was oxidized in order thus to obtain the oligomeric product. The residual protective groups were then removed, and the product was purified and desalted by means of HPLC.

The described process of Eschenmoser et al. (1993, supra), however, shows the following disadvantages:

1. The use of non-anomerically pure tetrabenzoylpentopyranoses (H. G. Fletcher, J. Am. Chem. Soc. 1955, 77, 5337) for the nucleosidation reaction with nucleobases reduces the yields of the final product owing to the necessity of rigorous chromatographic cuts in the following working steps.
2. With five reaction stages, starting from ribopyranoses which have a nucleobase in the 1'-position, up to the protected 3'-benzoates, the synthesis is very protracted and carrying-out on the industrial scale is barely possible. In addition to the high time outlay, the yields of monomer units obtained are low: 29% in the case of the purine unit adenine, 24% in the case of the pyrimidine unit uracil.

3. In the synthesis of the oligonucleotides, 5-(4-nitrophenyl)-1H-tetrazole is employed as a coupling reagent in the automated p-RNA synthesis. The concentration of this reagent in the solution of tetrazole in acetonitrile is in this case so high that the 5-(4-nitrophenyl)-1H-tetrazole regularly crystallizes out in the thin tubing of the synthesizer and the synthesis thus comes to a premature end. Moreover, it was observed that the oligomers were contaminated with 5-(4-nitrophenyl)-1-tetrazole.
4. The described work-up of p-RNA oligonucleotides, especially the removal of the base-labile protective groups with hydrazine solution, is not always possible if there is a high thymidine fraction in the oligomers.

A biomolecule, e.g. DNA or RNA, can be used for non-covalent linking with another biomolecule, e.g. DNA or RNA, if both biomolecules contain sections which, as a result of complementary sequences of nucleobases, can bind to one another by formation of hydrogen bridges. Biomolecules of this type are used, for example, in analytical systems for signal amplification, where a DNA molecule whose sequence is to be analysed is on the one hand to be immobilized by means of such a non-covalent DNA linker on a solid support, and on the other hand is to be bonded to a signal-amplifying branched DNA molecule (bDNA)(see, for example, S. Urdea, Biol/Technol. 1994, 12, 926 or U.S. Pat. No. 5,624,802). An essential disadvantage of the last-described systems is that to date they are subject with respect to sensitivity to the processes for nucleic acid diagnosis by polymerase chain reaction (PCR) (K. Mullis, Methods Enzymol. 1987, 155, 335). This is to be attributed, inter alia, to the fact that the non-covalent bonding of the solid support to the DNA molecule to be analysed as well as the non-covalent bonding of the DNA molecule to be analysed does not always take place specifically; as a result of which a mixing of the functions "sequence recognition" and "non-covalent bonding" occurs.

The object of the present invention was therefore to provide novel biomolecules and a process for their preparation in which the above-described disadvantages can be avoided.

The use of p-NAs as an orthogonal pairing system which does not intervene in the DNA or RNA pairing process solves this problem advantageously, as a result of which the sensitivity of the analytical processes described can be markedly increased.

One subject of the present invention is therefore the use of pentopyranosylnucleotides or pentopyranosylnucleic acids preferably in the form of a conjugate comprising a pentopyranosylnucleotide or a pentopyranosylnucleic acid and a biomolecule for the production of an electronic component, in particular in the form of a diagnostic.

Conjugates within the meaning of the present invention are covalently bonded hybrids of p-NAs and other biomolecules, preferably a peptide, protein or a nucleic acid, for example an antibody or a functional moiety thereof or a DNA and/or RNA occurring in its natural form. Functional moieties of antibodies are, for example, Fv fragments (Skerra & Plückthun (1988) Science 240, 1038), single-chain Fv fragments (scFv; Bird et al. (1988), Science 242, 423; Huston et al. (1988) Proc. Natl. Acad. Sci. USA, 85, 5879) or Fab fragments (Better et al. (1988) Science 240, 1041).

Biomolecule within the meaning of the present invention is understood as meaning a naturally occurring substance or a substance derived from a naturally occurring substance.

In a preferred embodiment, they are in this case p-RNA/DNA or p-RNA/RNA conjugates.

Conjugates are preferably used when the functions "sequence recognition" and "non-covalent bonding" must be realized in a molecule, since the conjugates according to the invention contain two pairing systems which are orthogonal to one another.

p-NAs and in particular the p-RNAs form stable duplexes with one another and in general do not pair with the DNAs and RNAs occurring in their natural form. This property makes p-NAs preferred pairing systems.

Such pairing systems are supramolecular systems of non-covalent interaction, which are distinguished by selectivity, stability and reversibility, and their properties are preferably influenced thermodynamically, i.e. by temperature, pH and concentration. On. account of their selective properties, such pairing systems can also be used, for example, as "molecular adhesive" for the bringing together of different metal clusters to give cluster associations having potentially novel properties [see, for example, R. L. Letsinger, et al., Nature 1996, 382, 607–9; P. G. Schultz et al., Nature 1996, 382, 609–11]. Consequently, the p-NAs are also suitable for use in the field of nanotechnology, for example for the production of novel materials, diagnostics and therapeutics and also microelectronic, photonic or optoelectronic components and for the controlled bringing together of molecular species to give supramolecular units, such as, for example, for the (combinatorial) synthesis of protein assemblies [see, for example, A. Lombardi, J. W. Bryson, W. F. DeGrado, Biomoleküls (Pept. Sci.) 1997, 40, 495–504], as p-NAs form pairing systems which are strongly and thermodynamically controllable. A further application therefore especially arises in the diagnostic and drug discovery field due to the possibility of providing functional, preferably biological units, such as proteins or DNA/RNA sections, with a p-NA code which does not interfere with the natural nucleic acids (see, for example, WO 93/20242).

Both sequential and convergent processes are suitable for the preparation of conjugates.

In a sequential process, for example after automated synthesis of a p-RNA oligomer has taken place directly on the same synthesizer—after readjustment of the reagents and of the coupling protocol—a DNA oligonucleotide, for example, is additionally synthesized. This process can also be carried out in the reverse sequence.

In a convergent process, for example, p-RNA oligomers having amino-terminal linkers and, for example, DNA oligomers having, for example, thiol linkers are synthesized in separate operations. An iodoacetylation of the p-RNA oligomer and the coupling of the two units according to protocols known from the literature (T. Zhu et al., Bioconjug. Chem. 1994, 5, 312) is then preferably carried. out. Convergent processes prove to be particularly preferred on account of their flexibility.

The term conjugate within the meaning of the present invention is also understood as meaning so-called arrays.

Arrays are arrangements of immobilized recognition species which, especially in analysis and diagnosis, play an important role in the simultaneous determination of analytes. Examples are peptide arrays (Fodor et al., Nature 1993, 364, 555) and nucleic acid arrays (Southern et al. Genomics 1992, 13, 1008; Heller, U.S. Pat. No. 5,632,957). A higher flexibility of these arrays can be achieved by binding the recognition species to coding oligonucleotides and the associated, complementary strands to certain positions on a solid carrier. By applying the coded recognition species to the "anti-coded" solid carrier and adjustment of hybridization conditions, the recognition species are non-covalently bonded to the desired positions. As a result, various types of recognition species, such as, for example, DNA sections, antibodies, can only be arranged simultaneously on a solid carrier by use of hybridization conditions (see FIG. 3). The prerequisite for this, however, are codons and anticodons which are extremely strong and selective—in order to keep the coding sections as short as possible—and do not interfere with natural nucleic acid necessary. p-NAs, preferably p-RNAs, are particularly advantageously suitable for this.

The term "carrier" within the meaning of the present invention is understood as meaning material, in particular chip material, which is present in solid or alternatively gelatinous form. Suitable carrier materials are, for example, ceramic, metal, in particular noble metal, glasses, plastics, crystalline materials or thin layers of the carrier, in particular of the materials mentioned, or (bio)molecular filaments such as cellulose, structural proteins.

The present invention therefore also relates to the use of pentopyranosylnucleic acids, preferably ribopyranosylnucleic acids for encoding recognition species, preferably natural DNA or RNA strands or proteins, in particular antibodies or functional moieties of antibodies. These can then be hybridized with the appropriate codons on a solid carrier according to FIG. 3. Thus arrays which are novel and diagnostically useful can always be built up in the desired positions on a solid carrier which is equipped with codons in the form of an array only by adjustment of hybridization conditions using combinations of recognition species which are always novel. If the analyte, for example a biological sample such as serum or the like, is then applied, the species to be detected are bonded to the array in a certain pattern which is then recorded indirectly (e.g. by fluorescence labelling of the recognition species) or directly (e.g. by impedance measurement at the linkage point of the codon). The hybridization is then eliminated by suitable conditions (temperature, salts, solvents, electrophoretic processes) so that again only the carrier having the codons remains. This is then again loaded with other recognition species and is used, for example, for the same analyte for the determination of another sample. The always new arrangement of recognition species in the array format and the use of p-NAs as pairing systems is particularly advantageous compared with other systems, see, for example, WO 96/13522 (see 16, below).

In a preferred embodiment, the pentopyranosylnucleoside is a compound of the formula (I)

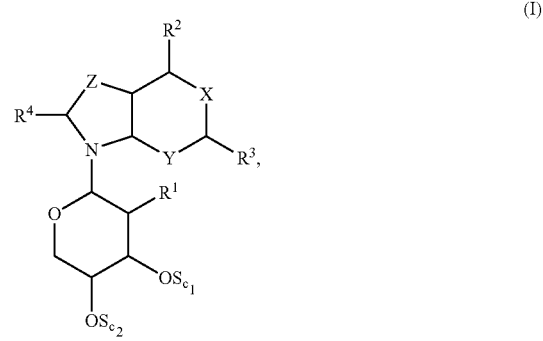

in which
$R^1$ is equal to H, OH, Hal where Hal is equal to Br or Cl or a radical selected from
or —O—P[N(i-Pr)$_2$]—(OCH$_2$CH$_2$CN)

where i-Pr is equal to isopropyl, $R^2$, $R^3$ and $R^4$ independently of one another, identically or differently, are in each case H, Hal where Hal is equal to Br or Cl, $NR^5R^6$, $OR^7$, $SR^8$, =O, $C_nH_{2n+1}$ where n is an integer from 1–12, preferably 1–8, in particular 1–4, a β-eliminable group, preferably a group of the formula —OCH$_2$CH$_2$R$^{18}$ where $R^{18}$ is equal to a cyano or p-nitrophenyl radical or a fluorenylmethyloxycarbonyl (Fmoc) radical, or $(C_nH_{2n})NR^{10}R^{11}$ where $R^{10}R^{11}$ is equal to H, $C_nH_{2n+1}$ or $R^{10}R^{11}$ linked via a radical of the formula

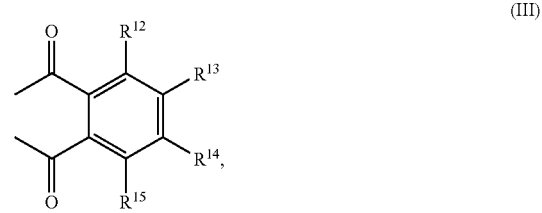

in which $R^{12}$, $R^{13}$, $R^{14}$ and $R^{15}$ independently of one another, identically or differently, are in each case H, $OR^7$, where $R^7$ has the abovementioned meaning, or $C_nH_{2n+1}$, or $C_nH_{2n-1}$, where n has the abovementioned meaning, and $R^5$, $R^6$, $R^7$ and $R^8$ independently of one another, identically or differently, is in each case H, $C_nH_{2n+1}$, or $C_nH_{2n-1}$, where n has the abovementioned meaning, —C(O)R$^9$ where $R^9$ is equal to a linear or branched, optionally substituted alkyl or aryl radical, preferably a phenyl radical, X, Y and Z independently of one another, identically or differently, is in each case =N—, =C(R$^{16}$)— or —N(R$^{17}$)— where $R^{16}$ and $R^{17}$ independently of one another, identically or differently, is in each case H or $C_nH_{2n+1}$ or $(C_nH_{2n})NR^{10}R^{11}$ having the abovementioned meanings, and $S_{c1}$ and $S_{c2}$ independently of one another, identically or differently, is in each case H or a protective group selected from an acyl, trityl or allyloxycarbonyl group, preferably a benzoyl or 4,4'-dimethoxytrityl (DMT) group,
or of the formula (II)

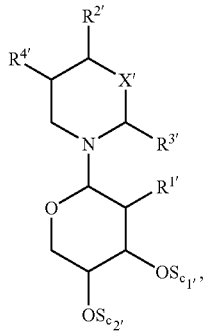

(II)

in which $R^{1'}$ is equal to H, OH, Hal where Hal is equal to Br or Cl, or a radical selected from
or —O—P[N(i-Pr)$_2$]—(OCH$_2$CH$_2$CN)
where i-Pr is equal to isopropyl,
$R^{2'}$, $R^{3'}$ and $R^{4'}$ independently of one another, identically or differently, is in each case H, Hal where Hal is equal to Br or Cl =O, $C_nH_{2n+1}$ or $C_nH_{2n-1}$, a β-eliminable group, preferably a group of the formula —OCH$_2$CH$_2$R$^{18}$ where $R^{18}$ is equal to a cyano or p-nitrophenyl radical or a fluorenylmethyloxycarbonyl (Fmoc) radical or $(C_nH_{2n})$ NR$^{10'}$R$^{11'}$, where $R^{10'}$, $R^{11'}$, independently of one another has the abovementioned meaning of $R^{10}$ or $R^{11}$, and
X', is in each case =N—, =C(R$^{16'}$)— or —N(R$^{17'}$)—, where $R^{16'}$ and $R^{17'}$ independently of one another have the abovementioned meaning of $R^{16}$ or $R^{17}$, and $S_{c1'}$ and $S_{c2'}$ have the abovementioned meaning of $S_{a1}$ and $S_{c2}$.

The pentopyranosylnucleoside is in general a ribo-, arabino-, lyxo- and/or xylopyranosylnucleoside, preferably a ribopyranosylnucleoside, where the pentopyranosyl moiety can be in the D configuration, but also in the L configuration.

Customarily, the pentopyranosylnucleoside according to the invention is a pentopyranosylpurine,-2,6-diaminopurine, -6-purinethiol, -pyridine, -pyrimidine, -adenosine, -guanosine, -isoguanosine, -6-thioguanosine, -xanthine, -hypoxanthine, -thymidine, -cytosine, -isocytosine, -indole, -tryptamine, -N-phthaloyltryptamine, -uracil, -caffeine, -theobromine, -theophylline, -benzotriazole or -acridine, in particular a pentopyranosylpurine, -pyrimidine, -adenosine, -guanosine, -thymidine, -cytosine, -tryptamine, -N-phthalotryptamine or -uracil.

The compounds also include pentopyranosylnucleosides which can be used as linkers, i.e. as compounds having functional groups which can bond covalently to biomolecules, such as, for example, nucleic acids occurring in their natural form or modified nucleic acids, such as DNA, RNA but also p-NAs, preferably pRNAs. This is surprising, as no linkers are yet known for p-NAs.

For example, these include pentopyranosylnucleosides in which $R^2$, $R^3$, $R^4$, $R^{2'}$, $R^{3'}$ and/or $R^{4'}$ is a 2-phthalimidoethyl or allyloxy radical. Preferred linkers according to the present invention are, for example, uracil-based linkers in which the 5-position of the uracil has preferably been modified, e.g.

N-phthaloylaminoethyluracil, but also indole-based linkers, preferably tryptamine derivatives, such as, for example, N-phthaloyltryptamine.

Surprisingly, by means of the present invention more easily handleable pentopyranosyl-N,N-diacylnucleosides, preferably purines, in particular adenosine, guanosine or 6-thioguanosine, are also made available, whose nucleobase can be completely deprotected in a simple manner. The invention therefore also includes pentopyranosylnucleosides in which $R^2$, $R^3$, $R^4$, $R^{2'}$, $R^{3'}$ and/or $R^{4'}$ is a radical of the formula —N[C(O)R$^9$]$_2$, in particular $N^6$, $N^6$-dibenzoyl-9-(β-D-ribopyranosyl)-adenosine.

It is furthermore surprising that the present invention makes available pentopyranosylnucleosides which carry a protective group, preferably a protective group which can be removed by base or metal catalysis, in particular an acyl group, particularly preferably a benzoyl group, exclusively on the 3'-oxygen atom of the pentopyranoside moiety. These compounds serve, for example, as starting substances for the direct introduction of a further protective group, preferably of an acid- or base-labile protective group, in particular of a trityl group, particularly preferably a dimethoxytrityl group, onto the 4'-oxygen atom of the pentopyranoside moiety without additional steps which reduce the yield, such as, for example, additional purification steps.

Moreover, the present invention makes available pentopyranosylnucleosides which carry a protective group, preferably an acid- or base-labile protective group, in particular a trityl group, particularly preferably a dimethoxytrityl group, exclusively on the 4'-oxygen atom of the pentopyranoside moiety. These compounds too serve, for example, as starting substances for the direct introduction of a further protective group, preferably of a protective group which can be removed by base or metal catalysis, in particular of an acyl group, particularly preferably of a benzoyl group, e.g. on the 2'-oxygen atom of the pentopyranoside moiety, without additional steps which reduce the yield, such as, for example, additional purification steps.

In general, the pentopyranosidenucleosides according to the invention can be reacted in a so-called one-pot reaction, which increases the yields and is therefore particularly advantageous.

The following compounds are preferred examples of the pentopyranosylnucleosides according to the invention:

A) [2',4'-Di-O-Benzoyl)-β-ribopyranosyl]nucleosides, in particular a [2',4'-di-O-benzoyl)-β-ribopyranosyl]-adenine, -guanine, -cytosine, -thymidine, -uracil, -xanthine or -hypoxanthine, and an N-benzoyl-2',4'-di-O-benzoyl-ribopyranosylnucleoside, in particular an -adenine, -guanine or -cytosine, and an N-isobutyroyl-2',4'-di-O-benzoylribopyranosylnucleoside, in particular an -adenine, -guanine or -cytosine, and an O$^6$-(2-cyanoethyl)-N$^2$-isobutyroyl-2',4'-di-O-benzoylribopyranosylnucleoside, in particular a -guanine, and an O$^6$ (2-(4-nitrophenyl) ethyl)-N$^2$-isobutyroyl-2,4'-di-O-benzoylribopyranosylnucleoside, in particular a -guanine.

B) β-Ribopyranosylnucleosides, in particular a β-ribopyranosyladenine, -guanine, -cytosine, -thymidine or -uracil, -xanthine or hypoxanthine, and an N-benzoyl-, N-isobutyroyl-, O$^6$-(2-cyanoethyl)- or O$^6$-(2-(4-nitrophenyl) ethyl)-N$^2$-isobutylroyl-β-ribopyranosylnucleoside.

C) 4'-DMT-pentopyranosylnucleosides, preferably a 4'-DMT-ribopyranosylnucleoside, in particular a 4'-DMT-ribopyranosyladenine, -guanine, -cytosine, -thymidine, -uracil, -xanthine or -hypoxanthine, and an N-benzoyl-4'-DMT-ribopyranosylnucleoside, in particular an N-benzoyl-4'-DMT-ribopyranosyladenine, -guanine or -cytosine, and an N-isobutyroyl-4'-DMT-ribopyranosylnucleoside, in particular an N-isobutyroyl-4'-DMT-ribopyranosyladenine, -guanine or -cytosine and an $O^6$-(2-cyanoethyl)-$N^2$-isobutyroyl-4'-DMT-ribopyranosylnucleoside, in particular an $O^6$-(2-cyanoethyl)-$N^2$-isobutyroyl-4'-DMT-ribopyranosylguanine, and an $O^6$-2-(-4-nitrophenyl)ethyl)-$N^2$-isobutyroyl-4'-DMT-ribopyranosylnucleoside, in particular an $O^6$-(2-(-4-nitrophenyl)ethyl)-$N^2$-isobutyroyl-4'-DMT-ribopyranosylguanine.

D) β-Ribopyranosyl-N,N'-dibenzoyladenosine or β-ribopyranosyl-N,N'-dibenzoylguanosine.

Suitable precursors for the oligonucleotide synthesis are, for example, 4'-DMT-pentopyranosylnucleoside-2'-phosphitamide/-H-phosphonate, preferably a 4'DMT-ribopyranosylnucleoside-2'-phosphitamide/-H-phosphonate, in particular a 4'-DMT-ribopyranosyladenine-, -guanine-, -cytosine-, -thymidine-, -xanthine-, hypoxanthine-, or -uracil-2'-phosphitamide/-H-phosphonate and an N-benzoyl-4'-DMT-ribopyranosyladenine-, -guanine- or -cytosine-2'-phosphitamide/-H-phosphonate and an N-isobutylroyl-4'-DMT-ribopyranosyladenine-, -guanine- or -cytosine-2'-phosphitamide/-H-phosphonate, $O^6$-(2-cyanoethyl)-4'-DMT-ribopyranosylguanine-, -xanthine-, -hypoxanthine-2'-phosphitamide/-H-phosphonate or $O^6$-(2-(4-nitrophenyl)ethyl)-$N^2$-isobutyroyl-4'-DMT-ribopyranosylguanine, and for the coupling to the solid carrier, for example, 4'-DMT-pentopyranosylnucleoside-2'-succinate, preferably a 4'-DMT-ribopyranosylnucleoside-2'-succinate, in particular a 4'DMT-ribopyranosyladenine-, -gaunine-, -cytosine-, thymidine-, -xanthine-, -hypoxanthine- or -uracil-2'-succinate and an N-benzoyl-4'-DMT-ribopyranosyladenine-, -guanine- or -cytonsine-2'-succinate and an N-isobutyroyl-4'-DMT-ribopyranosyladenine-, -guanine- or -cytosine-2'-succinate, O-(2-cyanoethyl)-4'-DMT-ribopyranosylguanine succinate and an $O^6$-(2-(4-nitrophenyl)ethyl)-$N^2$-isobutyroyl-4'-DMT-ribopyranosylguanine-2'-succinate.

The pentapyranosylnucleosides can be particularly advantageously prepared according to the present invention in that, starting from the unprotected pentopyranoside, (a) in a first step the 2'-, 3'- or 4'-position of the pentopyranoside is first protected, and preferably (b) in a second step the other position is protected on the 2'-, 3'- or 4'-position.

This process is not restricted to the nucleobases described in the cited literature, but can surprisingly be carried out successfully using a large number of natural and synthetic nucleobases. Moreover, it is particularly surprising that the process according to the invention can be carried out in high yields and with a time saving of on average 60% in comparison with the process known from the literature, which is particularly advantageous for industrial application. In addition, using the process according to the invention the purification steps necessary in the process described in the literature, e.g. chromatographic intermediate purifications, are not necessary and the reactions can in some cases be carried out as a so-called one-pot reaction, which markedly increases the space/time yields.

In a particular embodiment, in the case of a 2'-protected position a rearrangement of the protective group from the 2'-position to the 3'-position takes place, which in general is carried out in the presence of a base, in particular in the presence of N-ethyldiisopropylamine and/or triethylamine. According to the present invention, this reaction can be carried out particularly advantageously in the same reaction container as the one-pot reaction.

In a further preferred embodiment, the pyranosylnucleoside is protected by a protective group $S_{c1}$, $S_{c2}$, $S_{c1'}$ or $S_{c2'}$ which is acid-labile, base-labile or can be removed with metal catalysis, the protective groups $S_{c1}$ and $S_{c1'}$ preferably being different from the protective groups $S_{c2}$ and $S_{c2'}$.

In general, the protective groups mentioned are an acyl group, preferably an acetyl, benzoyl, nitrobenzoyl and/or methoxybenzoyl group, trityl groups, preferably a 4,4'-dimethoxytrityl (DMT) group or a β-eliminable group, preferably a group of the formula —$OCH_2CH_2R^{18}$ where $R^{18}$ is equal to a cyano or p-nitrophenyl radical or a fluorenylmethyloxycarbonyl (Fmoc) group.

It is particularly preferred if the 2'- or 3'-position is protected by a protective group which is base-labile or can be removed with metal catalysis, preferably by an acyl group, in particular by an acetyl, benzoyl, nitrobenzoyl and/or methoxybenzoyl group, and/or the 4'-position is protected by an acid- or base-labile protective group, preferably by a trityl and/or Fmoc group, in particular by a DMT group.

Unlike the process known from the literature, this process consequently manages without acetal protective groups, such as acetals or ketals, which avoids additional chromatographic intermediate purifications and consequently allows the reactions to be carried out as one-pot reactions with surprisingly high space/time yields.

The protective groups mentioned are preferably introduced at low temperatures, as by this means they can be introduced surprisingly selectively.

Thus, for example, the introduction of a benzoyl group takes place by reaction with benzoyl chloride in pyridine or in a pyridine/methylene chloride mixture at low temperatures. A DMT group can be introduced, for example, by reaction with DMTCl in the presence of a base, e.g. of N-ethyldiisopropylamine (Hünig's base), and, for example, of pyridine, methylene chloride or a pyridine/methylene chloride mixture at room temperature.

It is also advantageous if after the acylation and/or after the rearrangement of the 2'- to the 3'-position which is optionally carried out, the reaction products are purified by chromatography. Purification after the tritylation is not necessary according to the process according to the invention, which is particularly advantageous.

The final product, if necessary, can additionally be further purified by crystallization.

For the preparation of a ribopyranosylnucleoside preferably first (a) a protected nucleobase is reacted with a protected ribopyranose, then (b) the protective groups are removed from the ribopyranosyl moiety of the product from step (a), and then (c) the product from step (b) is reacted according to the process described above in greater detail.

In this connection, in order to avoid further time- and material-consuming chromatography steps, it is advantageous only to employ anomerically pure protected pentopyranoses, such as, for example, tetrabenzoylpentopyranoses, preferably β-tetrabenzoylribopyranoses (R. Jeanloz, J. Am. Chem. Soc. 1948, 70, 4052).

In a further embodiment, a linker according to formula (II), in which $R^{4'}$ is $(C_nH_{2n})NR^{10'}R^{11'}$ and $R^{10'}R^{11'}$ is linked by means of a radical of the formula (III) having the meaning already designated, is advantageously prepared by the following process:

(a) a compound of the formula (II) where $R^{4'}$ is equal to $(C_nH_{2n})OS_{c3}$ or $(C_nH_{2n})Hal$, in which n has the above-mentioned meaning, $S_{c3}$ is a protective group, preferably a mesylate group, and Hal is chlorine or bromine, is reacted with an azide, preferably in DMF, then (b) the reaction product from (a), is preferably reduced with triphenylphosphine, e.g. in pyridine, then (c) the reaction product from (b) is reacted with an appropriate phthalimide, e.g. N-ethoxycarbonylphthalimide, and (d) the reaction product from (c) is reacted with an appropriate protected pyranose, e.g. ribose tetrabenzoate, and finally (e) the protected groups are removed, for example with methylate, and (f) the further steps are carried out as already described above.

In addition, indole derivatives as linkers have the advantage of the ability to fluoresce and are therefore particularly preferred for nanotechnology applications in which it may be a matter of detecting very small amounts of substance. Thus indole-1-ribosides have already been described in N. N. Suvorov et al., Biol. Aktivn. Soedin., Akad. Nauk SSSR 1965, 60 and Tetrahedron 1967, 23, 4653. However, there is no analogous process for preparing 3-substituted derivatives. In general, their preparation takes place via the formation of an aminal of the unprotected sugar component and an indoline, which is then converted into the indole-1-riboside by oxidation. For example, indole-1-glucosides and -1-arabinosides have been described (Y. V. Dobriynin et al. Khim.-Farm Zh. 1978, 12, 33), whose 3-substituted derivatives were usually prepared by means of Vielsmeier's reaction. This route for the introduction of aminoethyl units into the 3-position of the indole is too complicated, however, for industrial application.

In a further preferred embodiment, a linker according to formula (I), in which X and Y independently of one another, identically or differently, are in each case $=C(R^{16})$ where $R^{16}$ is equal to H or $C_nH_{2n}$ and $Z=C(R^{16})—$ where $R^{16}$ is equal to $(C_nH_{2n})NR^{10}R^{11}$ is therefore advantageously prepared by the following process:

(a) the appropriate indoline, e.g. N-phthaloyltryptamine, is reacted with a pyranose, e.g. D-ribose, to give the nucleoside triol, then (b) the hydroxyl groups of the pyranosyl moiety of the product from (a) are preferably protected with acyl groups, e.g. by means of acetic anhydride, then (c) the product from (b) is oxidized, e.g. by 2,3-dichloro-5,6-dicyanoparaquinone, and (d) the hydroxyl protective groups of the pyranosyl moiety of the product from (c) are removed, for example, by means of methylate and finally (e) the further steps as already described above are carried out.

This process, however, cannot only be used in the case of ribopyranoses, but also in the case of ribofuranoses and 2'-deoxyribofuranoses or 2'-deoxyribopyranoses, which is particularly advantageous. The nucleosidation partner of the sugar used is preferably tryptamine, in particular N-acyl derivatives of tryptamine, especially N-phthaloyl-tryptamine.

In a further embodiment, the 4'-protected, preferably, the 3',4'-protected pentopyranosylnucleosides are phosphitylated in a further step or bonded to a solid phase.

Phosphitylation is carried out, for example, by means of monoallyl N-diisopropylchlorophosphoramidite in the presence of a base, e.g. N-ethyldiisopropylamine or by means of phosphorus trichloride and imidazole or tetrazole and subsequent hydrolysis with addition of base. In the first case, the product is a phosphoramidite and in the second case an H-phosphonate. The bonding of a protected pentopyranosylnucleoside according to the invention to a solid phase, e.g. "long-chain alkylamino-controlled pore glass" (CPG, Sigma Chemie, Munich) can be carried out, for example, as described in Eschenmoser et al. (1993).

The compounds obtained serve, for example, for the preparation of pentopyranosylnucleic acids, in which, preferably (a) in a first step a protected pentopyranosylnucleoside is bonded to a solid phase as already described above and (b) in a second step the 3'-,4'-protected pentopyranosylnucleoside bonded to a solid phase according to step (a) is lengthened by a phosphitylated 3'-,4'-protected pentopyranosylnucleoside and then oxidized, for example, by an aqueous iodine solution, and (c) step (b) is repeated with identical or different phosphitylated 3'-,4'-protected pentopyranosylnucleosides until the desired pentopyranosylnucleic acid is present.

Acidic activators such as pyridinium hydrochloride, preferably benzimidazolium triflate, are suitable as a coupling reagent when phosphoramidites are employed, preferably after recrystallizing in acetonitrile and after dissolving in acetonitrile, as in contrast to 5-(4-nitrophenyl)-1H-tetrazole as a coupling reagent no blockage of the coupling reagent lines and contamination of the product takes place.

Arylsulphonyl chlorides, diphenyl chlorophosphate, pivaloyl chloride or adamantoyl chloride are particularly suitable as a coupling reagent when H-phosphonates are employed.

Furthermore, it is advantageous by means of addition of a salt, such as sodium chloride, to the protective-group-removing hydrazinolysis of oligonucleotides, in particular of p-NAs, preferably of p-RNAs, to protect pyrimidine bases, especially uracil and thymine, from ring-opening, which would destroy the oligonucleotide. Allyloxy groups can preferably be removed by palladium [Pd(0)] complexes, e.g. before hyrazinolysis.

In a further particular embodiment, pentofuranosyl-nucleosides, e.g. adenosine, guanosine, cytidine, thymidine and/or uracil occurring in their natural form, can also be incorporated in step (a) and/or step (b), which leads, for example, to a mixed p-NA-DNA or p-NA-RNA.

In another particular embodiment, in a further step an allyloxy linker of the formula $$S_{c4}NH(C_nH_{2n})CH(OPS_{c5}S_{c6})C_nH_{2n}S_{c7} \quad (IV)$$

in which $S_{c4}$ and $S_{c7}$ independently of one another, identically or differently, are in each case a protective group in particular selected from Fmoc and/or DMT,
$S_{c5}$ and $S_{c6}$ independently of one another, identically or differently, are in each case an allyloxy and/or diisopropylamino group, can be incorporated. n has the meaning already mentioned above.

A particularly preferred allyloxy linker is (2-(S)-N-Fmoc-$O^1$-DMT-$O^2$-allyloxydiisopropylaminophosphinyl-6-amino-1,2-hexanediol).

Starting from, for example, lysine, in a few reaction steps amino-terminal linkers can thus be synthesized which carry both an activatable phosphorus compound and an acid-labile protective group, such as DMT, and can therefore easily be used in automatable oligonucleotide synthesis (see, for example, P. S. Nelson et al., Nucleic Acid Res. 1989, 17, 7179; L. J. Arnold et al., WO 8902439). The repertoire was extended in the present invention by means of a lysine-based linker, in which instead of the otherwise customary cyanoethyl group on the phosphorus atom an allyloxy group was introduced, and which can therefore be advantageously employed in the Noyori oligonucleotide method (R. Noyori, J. Am. Chem. Soc. 1990, 112, 1691–6).

A further subject of the present invention also relates to an electronic component in particular in the form of a diagnostic, comprising an above-described pentopyranosylnucleoside or a pentopyranosylnucleoside in the form of a conjugate, and a process for the preparation of a conjugate, in which a pentopyranosylnucleoside or a pentopyranosylnucleic acid is combined with a biomolecule, as already described in detail above.

The following figures and examples are intended to describe the invention in greater detail, without restricting it.

EXAMPLES

Example 1

Figure 1:
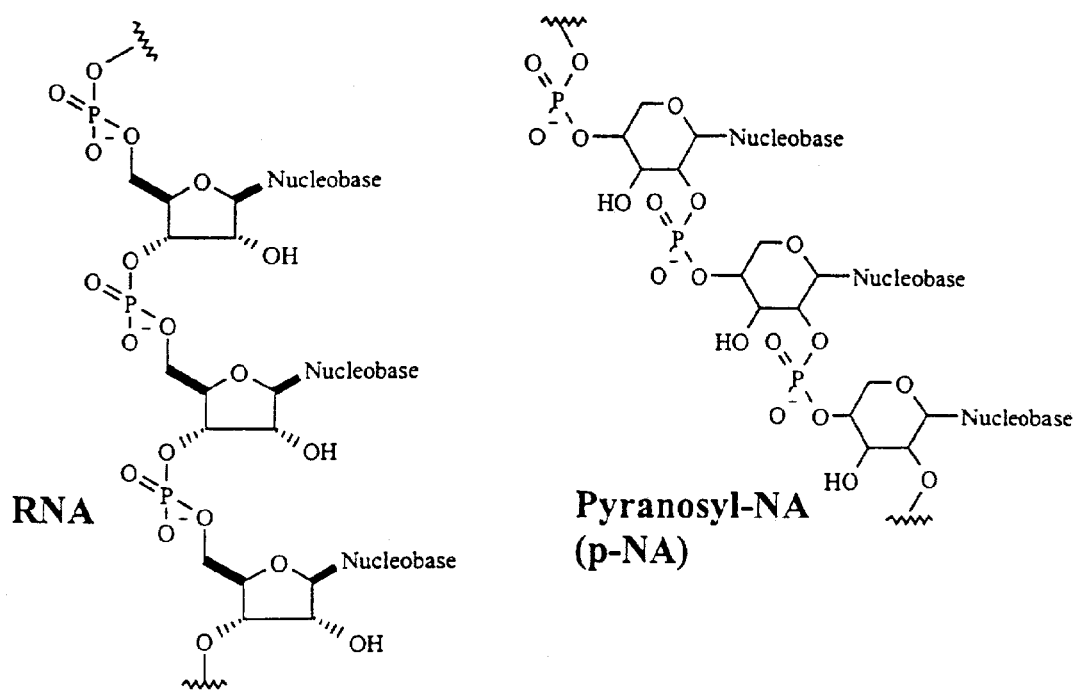
FIG. 1 shows a section of the structure of RNA in its naturally occurring form (left) and in the form of a p-NA (right).
Figure 2A:
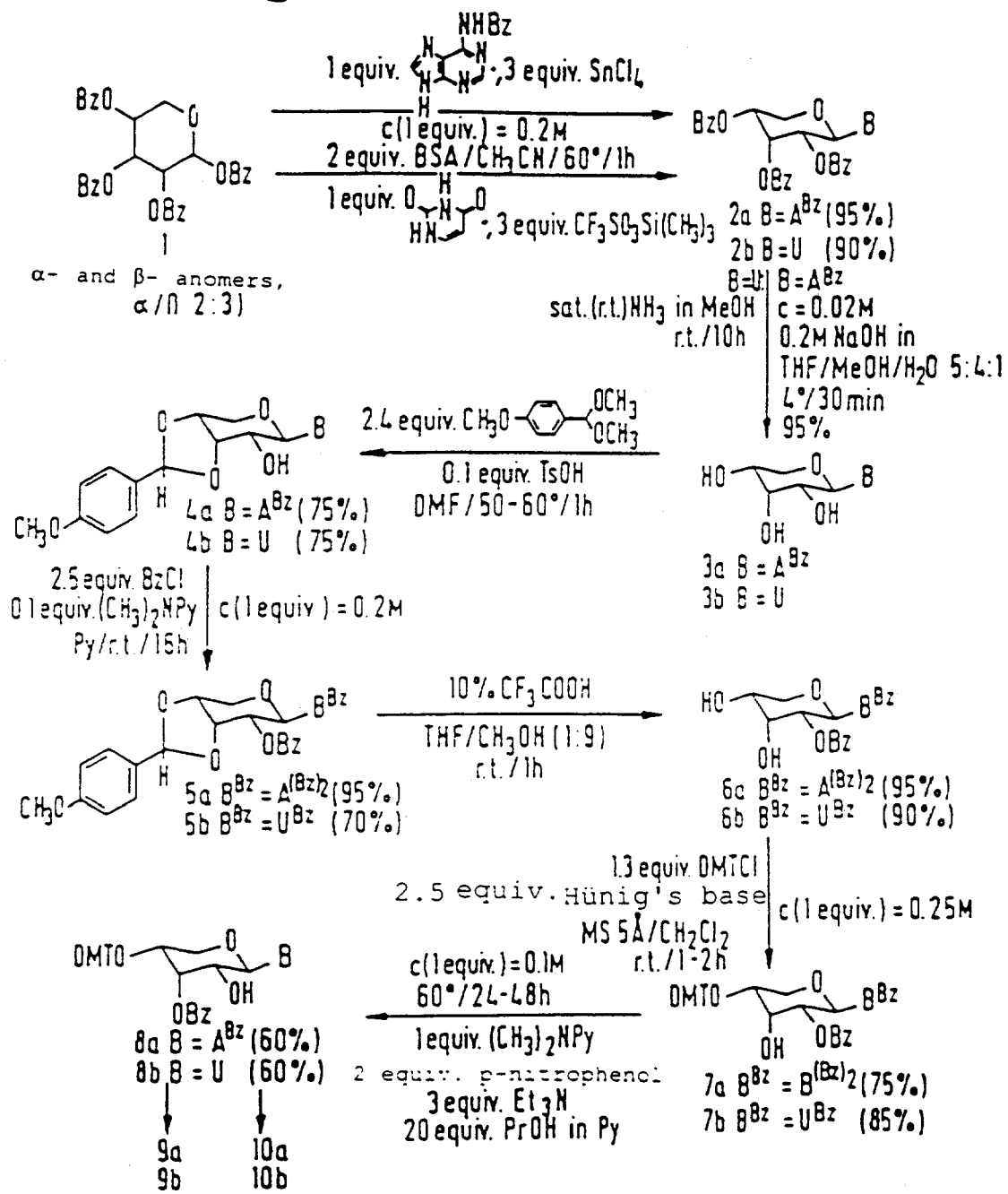
FIG. 2 schematically shows the synthesis of a p-ribo(A, U)-oligonucleotide according to Eschenmoser et al (1993).
Figure 2B:
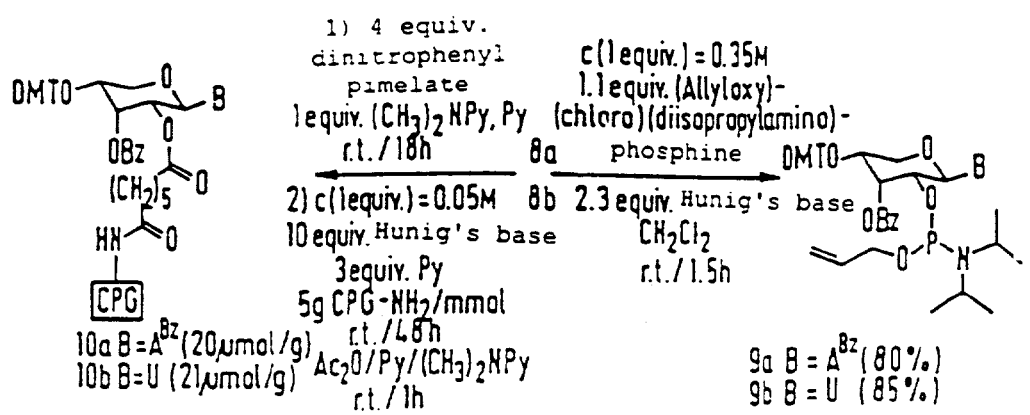
Figure 2B:
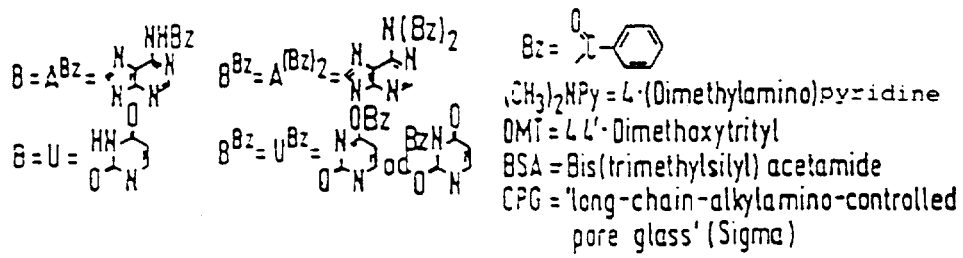
Figure 3:
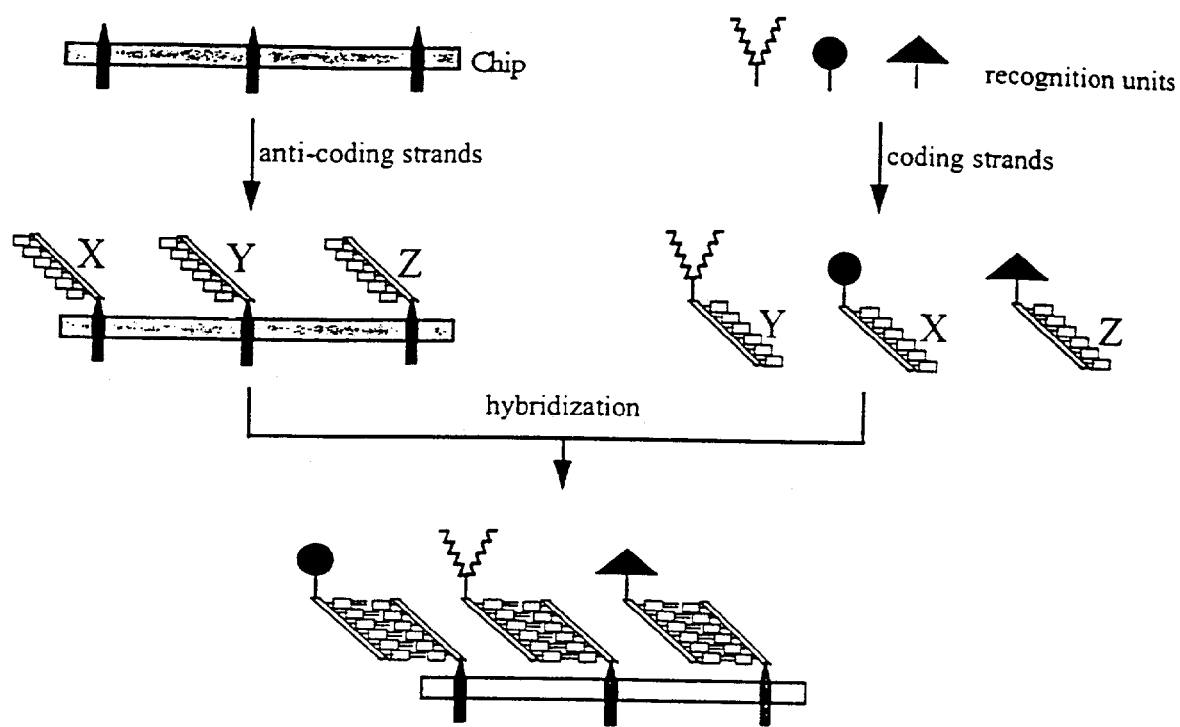
FIG. 3 schematically shows an arrangement of immobilized recognition structures (arrays) on a solid carrier.

Synthesis of 1-{3'-O-benzoyl-4'-O-[(4,4'-dimethoxytriphenyl)methyl]-β-D-ribopyranosyl}thymine First 4'-substitution, then 2'-substitution, then migration reaction:

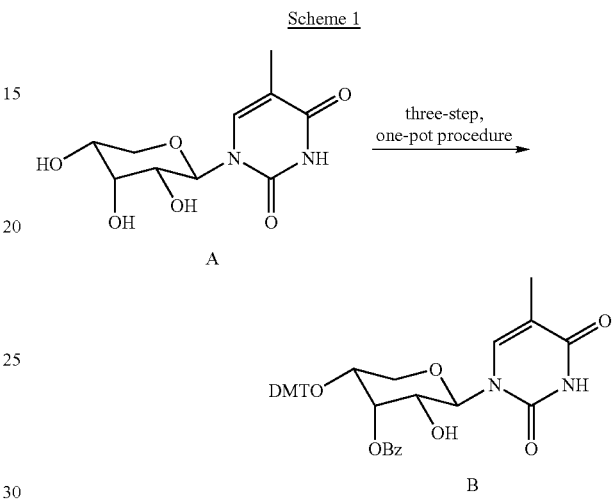

51.6 g (200 mmol) of 1-(β-D-ribopyranosyl)thymine A were dissolved in 620 ml of anhydrous pyridine under an argon atmosphere, 71.4 ml (2.1 eq.) of N-ethyldiisopropylamine and 100 g of molecular sieve (4 Å) were added and the mixture was stirred for 15 min using a KPG stirrer. 92 g (272 mmol; 1.36 eq.) of dimethoxytrityl chloride (DMTCl) were dissolved in 280 ml (freshly distilled from solid NaHCO$_3$) of chloroform and this solution was added dropwise to the triol solution at −6 to −50° C. in the course of 30 min. It was stirred at this temp. for 1 h, then stirred overnight at room temperature (RT.), cooled again, and a further 25 g (74 mmol; 0.37 eq.) of DMTCl in 70 ml of chloroform were added. The mixture was allowed to come to RT. and was stirred for 4 h.

A small sample was taken, subjected to aqueous work-up and chromatographed in order to obtain the analytical data of the 1-{4'-O-(4,4'-dimethoxytriphenyl)methyl]-β-D-ribopyranosyl}thymine:

$^1$H-NMR (300 MHz, CDCl3): 1.70 (bs, 2H, OH) ; 1.84 (d, 3H, Me); 2.90 (bs, 1H, OH); 3.18, 3.30 (2m, 2H, H(5')), 3.62 (bs, 1H, H(3')); 3.70–3.82 (m, 8H, 2 OMe, H(4'), H(2')); 5.75 (d, J=9.5 Hz, 1H, H(1')), 6.85 (m, 4H, Harom); 6.96 (m, 1H, Harom), 7.20 (m, 9H, Harom, H(6)), 8.70 (bs, 1H, H(3).)

The reaction mixture was treated with 2.46 g (20.5 mmol; 0.1 eq.) of 4-dimethylaminopyridine (DMAP), cooled to −6° C. and 27.9 ml (0.24 mol; 1.2 eq.) of benzoyl chloride (BzCl) in 30 ml of pyridine were added dropwise between −6 and −1° C. in the course of 15 min and the mixture was stirred for 10 min. To complete the reaction, a further 2.8 ml (24 mmol; 0.12 eq.) of BzCl were in each case added with cooling at an interval of 25 min and the mixture was finally stirred for 20 min.

460 ml of anhydrous pyridine, 841 ml (11.2 mol; 56 eq.) of n-propanol, 44 g (0.316 mol; 1.58 eq.) of p-nitrophenol, 21.7 g (0.18 mol; 0.9 eq.) of DMAP and 136 ml (0.8 mol; 4 eq.) of N-ethyldiisopropylamine were then added at RT. and the mixture was stirred at 61–63° C. for 48 h. The mixture was then allowed to stand at RT. for 60 h. The reaction mixture was again heated to 61–63° C. for 24 h, cooled to RT. and concentrated on a Rotavapor. The residue was taken up in 2 l of ethyl acetate, the molecular sieve was filtered off, the org. phase was extracted three times with 1 l of water each time and extracted once by stirring with 1.2 l of 10% strength citric acid and the org. phase was again separated off, extracted once with 1 l of water and finally with 1 l of saturated NaHCO$_3$ solution. The org. phase was dried using sodium sulphate, filtered and concentrated (220 g of residue).

The residue was first filtered through silica gel 60 (20×10 cm) using a step gradient of heptane/ethyl acetate, 1:1 to 0.1) for prepurification, then chromatographed on silica gel 60 (30×10 cm; step gradient of dichloromethane/ethyl acetate, 1:0 to 1:1).

The following were obtained:
40 g of non-polar fractions
52.9 g of 1-{3'-O-benzoyl-4'-O-[(4,4'-dimethoxytriphenyl)methyl]-β-D-ribopyranosyl}-thymine B
34.5 g of impure B
3.4 g of polar fractions The impure fraction was chromatographed again (SG 60, 45×10 cm; dichloromethane/ethyl acetate, 3:1) and yielded a further 11.3 g of B.

Total yield: 64.2 g (97 mmol) of B, i.e. 48% yield. $^1$H-NMR corresponds.

Example 2

Synthesis of N$^4$-benzoyl-1-{3'-O-benzoyl-4'-O-[(4,4'-dimethoxytriphenyl)methyl]-β-D-ribopyranosyl}cytosine First 2'-substitution, then 4'-substitution, then migration reaction:

All batches were carried out under an N$_2$ atmosphere.

N$^4$-Benzoyl-1-(2'-O-benzoyl-β-D-ribopyranosyl)cytosine 2

54.0 g (0.155 mol) of N$^4$-benzoyl-1-(β-D-ribopyranosyl) cytosine 1 were dissolved in 830 ml of dimethylformamide (DMF) and 1.5 l of pyridine (both solvents dried and stored over molecular sieve 3 Å) with warming to 124° C. 23.0 g (0.163 mol; 1.05 eq.) of BzCl, dissolved in 210 ml of pyridine, were added dropwise at −58° to −63° C. in the course of 3.5 h. The batch was stirred overnight in a cooling bath. 90.3 g (1.5 mol; 10 eq.) of n-propanol were stirred in and the batch was concentrated at 40° C. in a high vacuum. Pyridine residues were removed by twice adding 150 ml of toluene and concentrating again. 124.3 g of residue were dissolved in 500 ml of CH$_2$Cl$_2$, extracted twice by stirring with 300 ml of half-concentrated NaHCO$_3$ solution each time, and the precipitated solid was filtered off and dried: 60.7 g of residue. The CH$_2$Cl$_2$ phase was concentrated: 25.0 g. Separate chromatography on silica gel 60 (40×10 cm) with gradients (AcOEt/isohexane, 4:1, then pure AcOEt, then AcOET/MeOH, 19:1 to 2:1) yielded (TLC (silica gel, AcOET)):

| 16.8 g | of 2', 4' dibenzoate | (24%) | R$_f$ 0.5 |
| 12.4 g | of 1 | (23%) | R$_f$ 0.0 |
| 35.4 g | of 2 | (51%) | R$_f$ 0.14 |

N$^4$-Benzoyl-1-{3'-O-benzoyl-4'-O-[(4,4'-dimethyoxytriphenyl)methyl]-β-D-ribopyranosyl}cystosine 3

35.4 g (78 mmol) of 2 were dissolved in 390 ml of CH$_2$Cl$_2$ and 180 ml of pyridine (both anhydrous) and 0.94 g (7.8 mmol; 0.1 eq.) of DMAP, 34.6 ml (203 mmol; 2.6 eq.) of N-ethyldiisopropylamine and 33.1 g (98 mmol; 1.25 eq.) of DMTCl were added and the mixture was stirred at RT. for 2 h.

TLC (silica gel, AcOEt): R$_f$ 0.6.

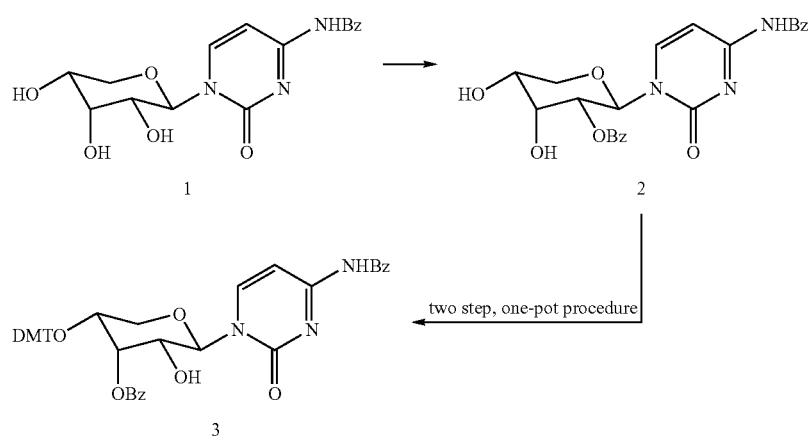

Scheme 2

$CH_2Cl_2$ was stripped off at 30° C., the residue was treated with 640 ml of pyridine, 9.37 g (78 mmol; 1.0 eq.) of DMAP, 32.5 ml (234 mmol; 3.0 eq.) of $Et_3N$, 21.7 g (156 mmol; 2.0 eq.) of p-nitrophenol and 93.8 g (1.56 mol; 20 eq.) of n-propanol and stirred at 65° C. for 42 h. The batch was concentrated in a high vacuum at 50° C., treated twice with 250 ml of toluene each time and concentrated. The residue was taken up in 1 l of $CH_2Cl_2$, extracted three times by stirring with 500 ml of dilute $NaHCO_3$ soln. each time, and the org. phase was dried using $Na_2SO_4$ and concentrated: 92.5 g of residue. Chromatography on silica gel 60 (50×10 cm) using gradients (methyl tert-butyl ether/isohexane, 2:1 to 4:1, then methyl tert-butyl ether/ AcOEt, 1:4, then AcOEt/MeOH, 1:1 to 1:3) yielded 44.7 g of product-containing fraction, which was recrystallized from 540 ml of $CH_2Cl_2$/methyl tert-butyl ether, 1:5. The crystallizate was recrystallized again from 300 ml of $CH_2Cl_2$/methyl tert-butyl ether, 1:1.

3: TLC (silica gel, $CHCl_3$/i-PrOH 49:1): $R_f$ 0.14.

The following was obtained: 30.0 g of $N^4$-benzoyl-1-{3'-O-benzoyl-4'-O[(4,4'-dimethoxytriphenyl)methyl]-β-D-ribopyranosyl}cytosine 3 i.e. 51% yield based on 2. $^1$H-NMR corresponds.

Example 3

Synthesis of $N^6$-benzoyl-9-(3'-O-benzoyl-4'-O-[(4,4'-dimethoxytriphenyl)methyl]-β-D-ribopyranosyl}adenine First 2'-substitution, then 4'-substitution, then migration reaction:

$^{13}$C-NMR (75 MHz, DMSQ): 65.0 (t, C(5')); 66.6 (s, C(4')), 68.1 (s, C(3'), 71.1 (s, C(2')), 79.6 (s, C(1')); 118.6 (C(5)); 139.5 (s, C(8)), 149.9 (s, C(4)), 152.5 (s, C(2)), 155.8 (s, C(6)).

$N^6,N^6$-Dibenzoyl-9-(β-D-ribopyranosyl)adenine 3

16.8 g (62.9 mmol) of 2 were suspended in 500 ml of anhydrous pyridine under an $N_2$ atmosphere and cooled to −4 to −10° C. 40 ml (199 mmol; 5 eq.) of trimethylchlorosilane were added dropwise in the course of 20 min and the mixture was stirred for 2.5 h with cooling.

36.5 ml (199 mmol; 5 eq.) of benzoyl chloride, dissolved in 73 ml of pyridine, were added at −10 to −15° C. in the course of 25 min, and stirred for 10 min with cooling and 2 h at RT. (TLC checking (silica gel, AcOEt/heptane 1:1): $R_f$ 0.5). The mixture was cooled again to −10° C., 136 ml of $H_2O$ (temp. max. +8° C.) were allowed to run in and the mixture was stirred overnight at RT. After conversion was complete, the solvent was stripped off and the residue was taken up twice in 200 ml of toluene each time and evaporated again. The mixture was treated with 500 ml each of $Et_2O$ and $H_2O$, stirred mechanically for 2 h, and the product which was only slightly soluble in both phases was filtered off, washed with $Et_2O$ and $H_2O$ and dried over $P_2O_5$ in a high vacuum: 23.8 g (80%) of 3.

TLC (silica gel, AcOEt/MeOH 9:1): $R_f$ 0.35.

$^1$H-NMR (300 MHz, DMSO): 3.60–3.80 (m, 3H, H(4'), H(5')); 4.06 (bs, 1H, H(3')); 4.30 (ddd, J=2.5, 8, 9.5 Hz, H(2')), 4.93 (d, J=6 Hz, 1H, OH), 5.20 (d, J=4 Hz, 1H, OH), 5.25 (d, J=4 Hz, 1H, OH), 5.77 (d, J=9.5 Hz, 1H, H(1')), 7.47

Scheme 3

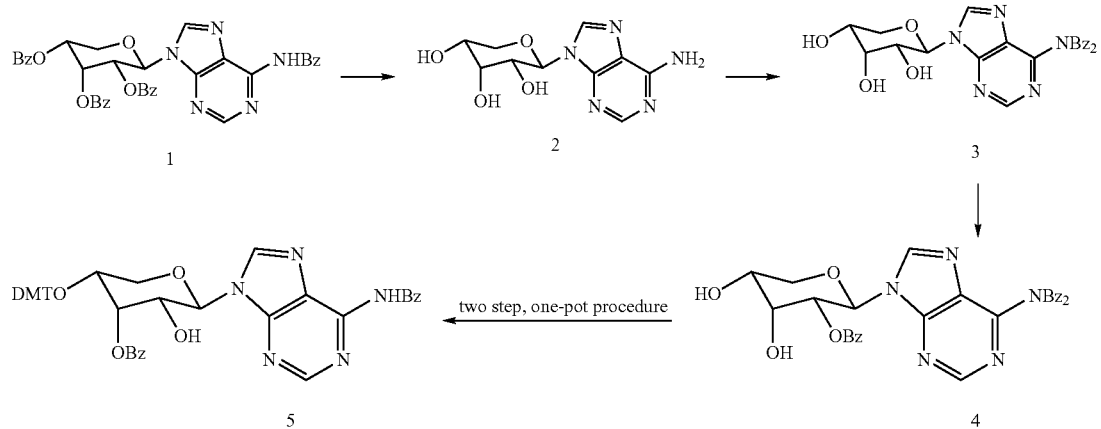

9-(β-D-Ribopyranosyl)adenine 2

68.37 g (100 mmol) of $N^6$-benzoyl-9-(2',3',4'-tri-O-benzoyl-β-D-ribopyranosyl)adenine 1 was stirred overnight at RT. in 300 ml of $NH_3$-saturated MeOH and the crystallizate was filtered off: 23.5 g (88%) of 2.

TLC (silica gel, AcOEt/MeOH 2:1): $R_f$ 0.23/$^1$H-NMR (300 MHz, DMSO): 3.56–3.78 (m, 3H, H(4'), H(5')); 4.04 (m, 1H, H(3')); 4.23 (ddd, J=2.5, 8, 9.5 Hz, H(2')), 4.89 (d, J=6 Hz, 1H, OH), 5.07 (d, J=7 Hz, 1H, OH), 5.12 (d, J=4 Hz, 1H, OH), 5.63 (d, J=9.5 Hz, 1H, H(1')), 7.22 (s, 2H, NH2), 8.14 (s, 1H, H(2)), 8.29 (s, 1H, H(8)).

(m, 4H, Harom), 7.60 (m, 2H, Harom), 7.78 (m, 4H, Harom), 8.70 (s, 1H, H—C(2), 8.79 (s, 1H, H(8)).

$^{13}$C-NMR (75 MHz, DMSO): 66.2 (t, C(5')); 66.5 (s, C(4')), 68.0 (s, C(3')), 71.0 (s, C(2')), 80.4 (s, C(1')); 112.42 (C(5)); 126.9 (s, C(5')), 126.9, 128.9, 133.3, 133.4 (arom. C), 146.0 (s, C(8)), 150.7 (s, C(4)), 151.8 (s, C(2)), 153.3 (s, C(6)) 172.0 (s, C=O)).

$N^6,N^6$-Dibenzoyl-9-(2'-O-benzoyl-β-D-ribopyranosyl)adenine 4

26.4 g (55,5 mmol) of 3 were dissolved in 550 ml of anhydrous $CH_2Cl_2$ and 55 ml of pyridine (in each case stored over a molecular sieve) under an N₂ atmosphere, treated with 0.73 g (5.55 mmol; 0.1 eq.) of DMAP and cooled to −87 to −90° C. 8.58 g (61 mmol; 1.1 eq.) of BzCl in 14 ml of pyridine were added dropwise in the course of 1 h and the mixture was left at −78° C. over a period of 60 h (week-end). The batch was concentrated, treated twice with 100 ml of toluene each time and evaporated in order to remove pyridine. Chromatography on silica gel 60 (20×10 cm) using gradients (AcOEt/heptane, 1:1 to 9:1) yielded 23.2 g of 4.

¹H-NMR corresponds. Time saving compared with process known from the literature: 50%.

Example 4

Synthesis of 9-[3'-O-benzoyl-4'-O-((4,4'-dimethoxytriphenyl)methyl)-β-D-ribopyranosyl]-2-O-allyl-2-N-isobutyroylguanine First 3'-substitution, then 4'-substitution:

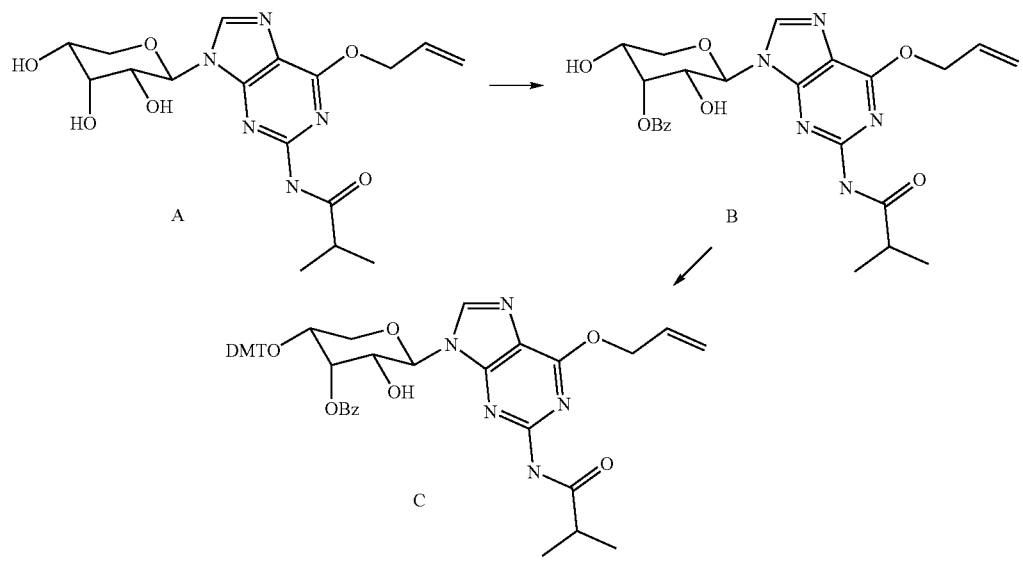

4: TLC (silica gel, AcOEt): R_f 0.34.

N⁶-Benzoyl-9-{3'-O-benzoyl-4'-O-[(4,4'-dimethoxytriphenyl)methyl]-β-D-ribopyranosyl}adenine 5

23.2 g (40 mmol) of 4 were dissolved in 160 ml of anhydrous CH₂Cl₂ and subsequently treated with 14.9 g (56 mmol; 1.1 eq.) of DMTCl and 17.7 ml (104 mmol; 2.6 eq.) of N-ethyldiisopropylamine. After stirring at RT for 2 h, a further 4.0 g (11.8 mmol; 0.3 eq.) of DMTCl were added and the mixture was stirred for a further 40 min. The batch was concentrated in a Rotavapor at 350–520 mbar and 35° C.
TLC (silica gel, AcOEt/heptane 1:1): R_f 0.18.

The residue was dissolved in 260 ml of anhydrous pyridine and subsequently treated with 51 ml (679 mmol; 17 eq.) of n-propanol, 16.6 ml (120 mmol; 3 eq.) of Et₃N, 11.1 g (80 mmol; 2 eq.) of p-nitrophenol and 5.3 g (44 mmol; 1.1 eq.) of DMAP and stirred at 60–63° C. for 23 h. The batch then remained at RT. for 21 h. The reaction mixture was concentrated in a Rotavapor. The residue was treated twice with 200 ml of toluene each time and concentrated, dissolved in CH₂Cl₂ and extracted three times with water.
Chromatography on silica gel 60 (30×10 cm) using gradients (AcOEt/heptane, 1:2 to 1:0; then AcOEt/MeOH, 1:0 to 9:1) yielded 13 g of 5.

5: TLC (silica gel, AcOEt/heptane 4:1): R_f 0.2.

The following was obtained: 13 g of N⁶-benzoyl-9-{3'-O-benzoyl-4'-O-[(4,4'-dimethoxytriphenyl)methyl-β-D-ribopyranosyl}adenine 5 i.e. 30% yield based on 3.

9-[3'-O-Benzoyl-β-D-ribopyranosyl]-2-O-allyl-2-N-isobutyroylguanine B

The G triol A (393 mg, 1.0 mmol) was dissolved in 4 ml of dry dichloromethane. The solution was treated with trimethyl orthobenzoate (0.52 ml, 3.0 mmol) and camphorsulphonic acid (58 mg, 0.25 mmol) and stirred for 15 h at room temperature. The mixture was then cooled to 0° C. and treated with 2 ml of mixture of acetonitrile, water and trifluoroacetic acid (50:5:1), which was precooled to 0° C. The mixture was stirred for 10 min and the solvent was removed in vacuo. The residue was purified by flash chromatography on silica gel (2.3×21 cm) using dichloromethane/methanol 100:3. 25 mg (5%) of 4-O-benzoyl compound 139 mg (28%) of mixed fractions and 205 mg (41%) of the desired 3-O-benzoyl compound B were obtained.

¹H-NMR (300 MHz, CDCl₃): 1.12, 1.14 (2d, J=7.0 Hz, 2×3H, NHCOCHMe₂), 2.78 (hep, J=7 Hz, 1H, NHCOCH Me₂), 3.85 (dd, J=6.0, 11.0 Hz, 1H, H-5'_eq), 3.94 (app. T, J=11.0 Hz, 1H, H=5'_ax), 4.12 (ddd, J=2.5, 6.0, 11.0 Hz, 1H, H-4'), 4.52 (dd, J=3.5, 9.5 hz, 1H, H-2'), 5.00 (dt, J=1.5, 6.0 Hz, 2H, All), 5.19 (dq, J=1.5, 10.0 Hz, 1H, All), 5.39 (dq, 1.5, 16.5 Hz, 1H, All), 5.85 (bt, J=3.0 Hz, 1H, H-3'), 5.97 (d, J=9.5 Hz, 1H, H-1'), 6.07 (ddd, J=6.0, 10.0, 16.5 Hz, 1H, All) 7.40–7.58 (m, 3H. Bz), 8.10–8.16 (m, 2H, Bz), 8.28 (s, 1H, H-8).

9-[3'-O-Benzoyl-4'-O-((4,4'-dimethyloxytriphenyl) methyl)-β-D-ribopyranosyl]-2-O-allyl-2-N-isobutyroylguanine C The diol B (101 mg, 0.2 mmol) was suspended in 3.2 ml of dry dichloromethane. The suspension was treated with 171 μl (1.0 mmol) of N-ethyldiisopropylamine, 320 μl (3.96 mmol) of pyridine and 102 mg (0.3 mmol) of DMTCl and stirred at room temperature. After 24 h, a further 102 mg (0.3 mmol) of DMTCl were added and the mixture was again stirred for 24 h. It was then diluted with 30 ml of dichloromethane. The solution was washed with 20 ml of 10% strength aqueous citric acid solution and 10 ml of saturated sodium bicarbonate solution, dried over MgSO₄ and concentrated in vacuo. The residue was purified by flash chromatography on silica gel (2.3×20 cm) using dichloromethane/methanol 100:1. 39 mg of the known, desired product C (24%) were obtained.

Example 5

Synthesis of p-RNA Linker Systems

Three ways are described below which make possible the provision of linkers which have an amino terminus, which can then be used for the linkage of functional units:

5.1 Uracil-based Linker on the basis of the modification of the 5-position of the uracil.

The preparation of hydroxyethyluracil 28 is possible on a large scale according to a known method (J. D. Fissekis, A. Myles, G. B. Brown, J. Org. Chem. 1964, 29, 2670). g-Butyrolactone 25 was formylated with methyl formate, the sodium salt 26 was reacted to give the urea derivative 27 and this was cyclized to give the hydroxyethyluracil 28 (Scheme 4).

Scheme: 4
Synthesis of hydroxyethyluracil 28.

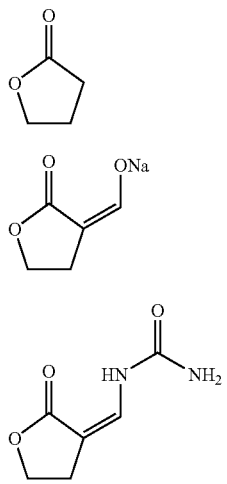

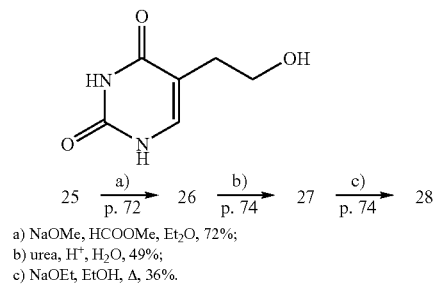

25 →a) p. 72→ 26 →b) p. 74→ 27 →c) p. 74→ 28 a) NaOMe, HCOOMe, Et₂O, 72%;
b) urea, H⁺, H₂O, 49%;
c) NaOEt, EtOH, Δ, 36%.

Scheme 5:
Synthesis of N-phthaloylaminoethyluracil 32.

28 →a) p. 77→ 29 →b) p. 80→ 30 →c) p. 82→ 31 →d) p. 84→ 32 a) MsCl, py, 0°, 50%;
b) NaN₃, DMF, 60°, 71%;
c) 1. PPh₃, py; 2. NH₃/H₂O, 85%;
d) PhtNCO₂Et, Na₂CO₃, H₂O, 91%.

Hydroxyethyluracil 28 was mesylated with methanesulphonyl chloride in pyridine to give 29 (J. D. Fissekis, F. Sweet, J. Org. Chem. 1973, 38, 264).

The following stages have been newly invented: using sodium azide in DMF, 29 was reacted to give the azide 30 and this was reduced with triphenylphosphine in pyridine to give the aminoethyluracil 31. The amino function in 31 was finally protected with N-ethyoxycarbonylphtalimide (Scheme 5). Nucleosidation of ribose tetrabenzoate 33 with N-phtaloylaminoethyluracil 32 yielded the ribose tribenzoate 34 in good yields. The anomeric centre of the pyranose ring, as can be clearly seen from the coupling constant between H—C(1') and H—C(2') of J=9.5 Hz, has the β configuration. Subsequent removal of the benzoate protective groups with NaOMe in MeOH yielded the linker triol 35. 35 was reacted with benzoyl chloride at −78° C. in pyridine/dichloromethane 1:10 in the presence of DMAP. In this process, in addition to the desired 2'-benzoate 36 (64%), 2',4'-dibenzoylated product (22%) was obtained, which was collected and converted again into the triol 35 analogously to the methanolysis of 34 to, 35. The 2'-benzoate 36 was tritylated in the 4'-position in yields. of greater than 90% using dimethoxytrityl chloride in the presence of Hünig's base in dichloromethane. The rearrangement of 4'-DMT-2'-benzoate 37 to the 4'-DMT-3'-benzoate 38 was carried out in the presence of DMAP, p-nitrophenol and Hünig's base in n-propanol/pyridine 5:2. After chromatography, 38 is obtained. 4'-DMT-3'-benzoate 38 was finally reacted with ClP(OAll)N(iPr)$_2$ in the presence of Hünig's base to give the phosphoramidite 39 (Scheme 6). This can be employed for the automated oligonucleotide synthesis without changing the synthesis protocol.

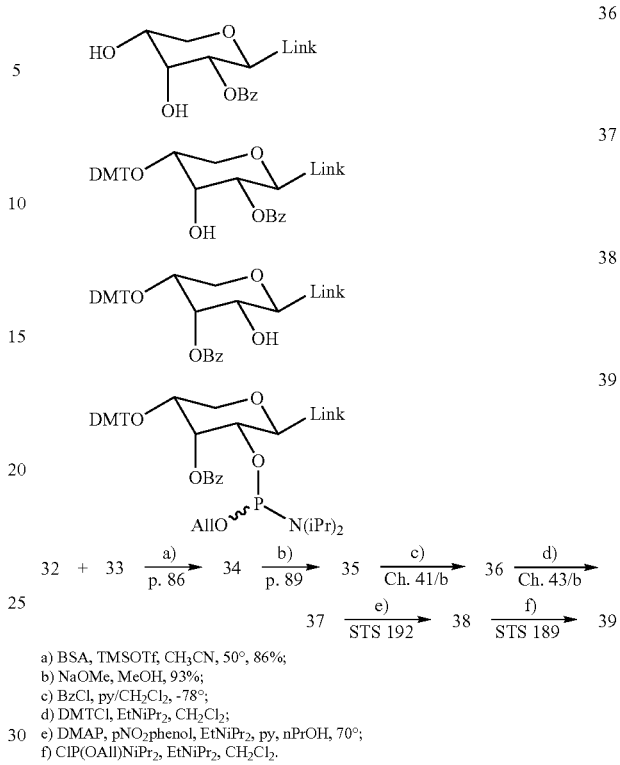

a) BSA, TMSOTf, CH$_3$CN, 50°, 86%;
b) NaOMe, MeOH, 93%;
c) BzCl, py/CH$_2$Cl$_2$, -78°;
d) DMTCl, EtNiPr$_2$, CH$_2$Cl$_2$;
e) DMAP, pNO$_2$phenol, EtNiPr$_2$, py, nPrOH, 70°;
f) ClP(OAll)NiPr$_2$, EtNiPr$_2$, CH$_2$Cl$_2$.

Procedure

Synthesis of a Uracil Linker Unit 5-(2-Azidoethyl)uracil (30)

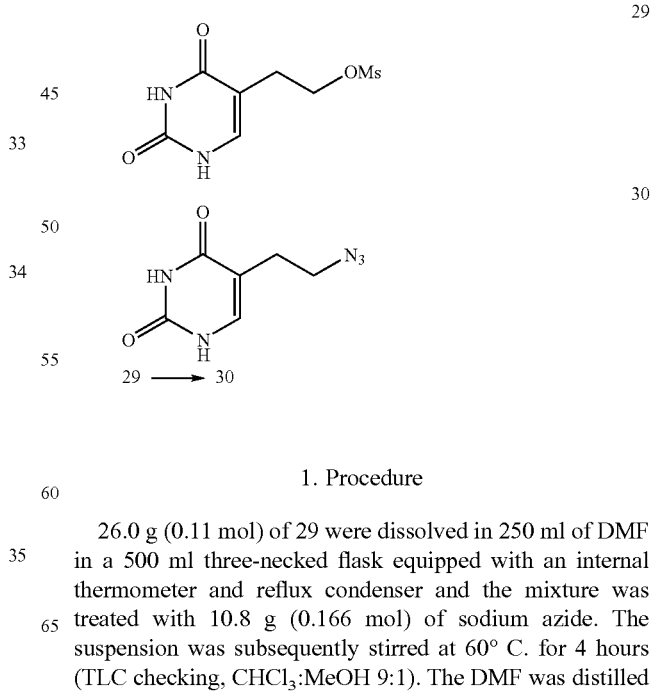

1. Procedure 26.0 g (0.11 mol) of 29 were dissolved in 250 ml of DMF in a 500 ml three-necked flask equipped with an internal thermometer and reflux condenser and the mixture was treated with 10.8 g (0.166 mol) of sodium azide. The suspension was subsequently stirred at 60° C. for 4 hours (TLC checking, CHCl$_3$:MeOH 9:1). The DMF was distilled Scheme 6:
Synthesis of the linker phosphoramidite 39.

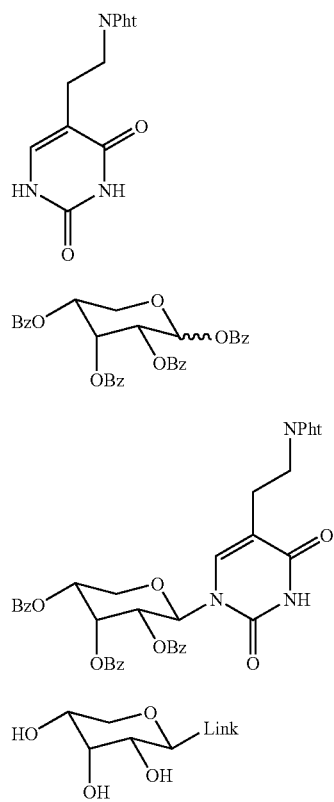

off and the residue was stirred with 150 ml of water. The solid was filtered off, washed with about 50 ml of water and dried overnight over phosphorus pentoxide in vacuo in a desiccator. 14.2 g (71%) of 30 were obtained in the form of a colourless solid of m.p. 230–235° C. (with dec.).

2. Analytical Data 5-(2-Azidoethyl)uracil (30)

| M.p. | 230–235° C. with decomp. |
|---|---|
| TLC: | CHCl$_3$/MeOH 9:1, R$_f$ 0.48 |
| UV (MeOH): | λ$_{max}$ 263.0 (7910). |
| IR (KBr): | 3209s, 3038s, 2139s, 1741s, 1671s, 1452m, 1245m, 1210m |
| $^1$H-NMR (300 MHz, d$_6$-DMSO): | 2.46 (t, 2H, J(CH$_2$CH$_2$N, CH$_2$CH$_2$N) = 7.0, CH$_2$CH$_2$N); 3.40 (t, 2H, J(CH$_2$CH$_2$N, CH$_2$CH$_2$N) = 7.0 CH$_2$CH$_2$N); 7.36 (s, H—C(6)); 11.00 (br. s, 2H, H—N(1), H—N(3). |
| MS (ESI$^+$): | 180.0 [M + H]. . |

5-(2-Aminoethyl)uracil (31)

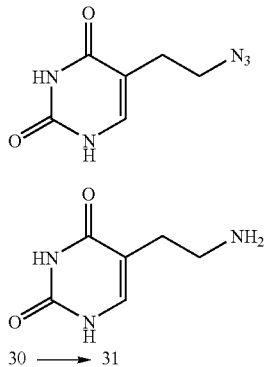

30 → 31

1. Procedure 14.2 g (78.0 mmol) of 30 were suspended in 175 ml of pyridine in a 250 ml three-necked flask equipped with an internal thermometer and reflux condenser and the mixture was treated with 61.4 g (234 mmol) of triphenylphosphine[2)]. It was heated at 60° C. for 5 hours and stirred overnight at room temp. (TLC checking, CHCl$_3$/MeOH 5:1). 40 ml of 25% strength ammonia solution were added to the suspension, which then clarified. The solvents were removed in vacuo in a rotary evaporator. The residue was stirred at room temp. for 30 min in 200 ml of CH$_2$Cl$_2$/MeOH 1:1, and the precipitate was filtered off and washed with CH$_2$Cl$_2$. After drying in vacuo in a desiccator over phosphorus pentoxide, 10.0 g (85%) of 31 of m.p. 214–220° C. were obtained.

2. Analytical Data 5-(2-Aminoethyl)uracil (31)

| M.p. | 214–220° C. with evolution of gas, presintering. |
|---|---|
| TLC: | CHCl$_3$/MeOH/HOAc/H$_2$O 85:20:10:2, R$_f$ 0.07 |
| UV (MeOH): | λ$_{max}$ 263.0 (6400). |
| IR (KBr): | 3430m, 3109s, 1628s, 1474m, 1394s, 1270s, 1176w, 1103m, 1021m, 966m, 908m, 838m. |
| $^1$H-NMR (300 MHz, d$_6$-DMSO): | 2.21 (t, 2H, J(CH$_2$CH$_2$N, CH$_2$CH$_2$N) = 6.8, CH$_2$CH$_2$N); 2.59 (t, 2H, J(CH$_2$CH$_2$N, CH$_2$CH$_2$N) = 6.8 CH$_2$CH$_2$N); 5.90 (v. br. s, 4H, H—N(1), H—N(3), NH$_2$); 7.19 (s, H—C(6)). |
| MS (ESI$^-$): | 153.9 [M − H]. |

5-(2-Phtalimidoethyl)uracil (32)

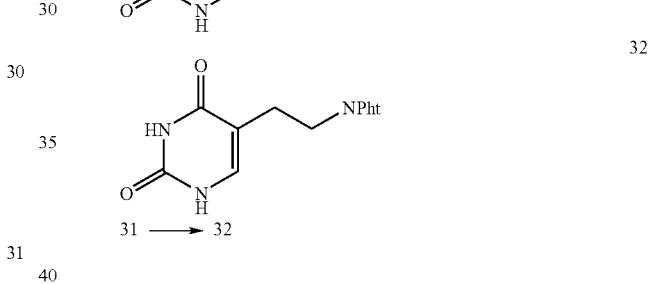

31 → 32

1. Procedure 9.6 g (61.8 mmol) of 31 were suspended in 100 ml of water in a 250 ml round-bottomed flask and treated with 6.64 g (62.6 mmol) of Na$_2$CO$_3$. After stirring at room temp. for 15 min, 14.3 g (65 mmol) of N-ethoxycarbonylphtalimide were added in portions and the mixture was stirred for three hours at room temp. (TLC checking, CHCl$_3$/MeOH 5:1). The now viscous, white suspension was carefully[1)] adjusted to pH 4 using conc. hydrochloric acid and the white precipitate was filtered off. After washing with water, the solid was dried over phosphorus pentoxide in a desiccator in vacuo. This yielded 16.0 g (91%) of 32 of m.p. 324–327° C.

2. Analytical Data 5-(2-Phtalimidoethyl)uracil (32)

| M.p. | 324–327° C. with decomp. |
|---|---|
| TLC: | CHCl$_3$/MeOH 5:1, R$_f$ 0.51 |
| UV (MeOH): | λ$_{max}$ 263.0 (5825); λ 298.0 (sh., 1380). |

-continued

| | |
|---|---|
| IR (KBr): | 3446m, 3216m, 1772m, 1721s, 1707s, 1670s, 1390m. |
| $^1$H-NMR (300 MHz, d$_6$-DMSO): | 2.49 (t, 2H, J(CH$_2$CH$_2$N, CH$_2$CH$_2$N) = 6.0, CH$_2$CH$_2$N); 3.71 (t, 2H, J(CH$_2$CH$_2$N, CH$_2$CH$_2$N) = 6.0 CH$_2$CH$_2$N); 7.24 (s, H—C(6)); 7.84 (m$_c$, 4H, NPht); 10.76 (br, s, H—N(1), H—N(3)). |
| MS (ESI$^-$): | 284.0 [M – H]. |

1-(2,3,4-Tri-O-benzoyl-β-D-ribopyranosyl)-5-(2-phtalimidoethyl)uracil (34)

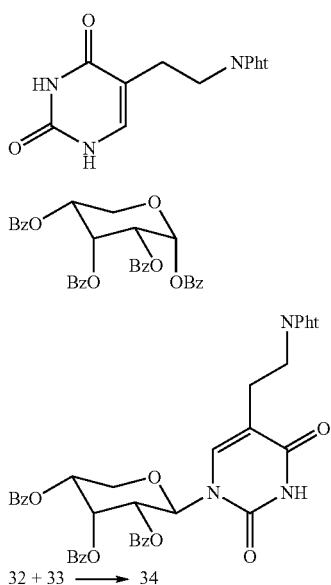

32 + 33 ⟶ 34

1. Procedure 7.00 g (24 mmol) of 32 and 13.6 g (24 mmol) of 33 were suspended in 120 ml of acetonitrile in a 250 ml three-necked flask, equipped with an argon lead-in, internal thermometer and septum. Firstly 12.2 ml (50 mmol) of BSA and, after stirring for 30 min, a further 7 ml (28 mmol) of BSA were then added by means of syringe. After heating to 40° C. for a short time, the reaction mixture clarified. 13 ml (72 mmol) of TMSOTf were added by means of syringe at room temp. After one hour, no product formation was yet observed (TLC checking, AcOEt/n-heptane 1:1). A further 13 ml (72 mmol) of TMSOTf were therefore added. Subsequently, the reaction mixture was heated to 50° C. After stirring at 50° C. for 2.5 h (TLC checking), the mixture was cooled to RT., [lacuna] onto an ice-cold mixture of 250 ml of AcOEt and 190 ml of satd. NaHCO$_3$ solution and intensively extracted by stirring for 10 min. It was again washed with 100 ml of NaHCO$_3$ solution and the aqueous phases were again extracted with 100 ml of AcOEt. The dil. org. phases were dried using MgSO$_4$ and the solvents were removed in vacuo in a rotary evaporator. After drying in an oil pump vacuum, 20.9 g of crude product were obtained. Chromatography on silica gel (h=25 cm, Φ=5 cm, AcOEt/n-heptane 1:1) yielded a TLC-uniform, foamy product, which was digested using Et$_2$O. Fitration and drying in an oil pump vacuum afforded 15 g (86%) of 34.

2. Analytical Data 1-(2,3,4-Tri-O-benzoyl-β-D-ribopyranosyl)-5-(2-phtalimidoethyl)uracil (34)

| | |
|---|---|
| M.p. | 124° C. (sintering) |
| TLC: | AcOEt/n-heptane 1:1, Rf 0.09. |
| UV (MeOH): | λ$_{max}$ 263.0 (11085): λ 299.0 (sh., 1530) |
| IR (KBr): | 3238w, 3067w, 1772m, 1710s, 1452m, 1395m, 1266s, 1110s, 1070m, 1026m. |
| $^1$H-NMR (300 MHz, CDCl$_3$): | 2.79 (m$_c$, 2H, CH$_2$CH$_2$N); 3.96 (m$_c$, 2H, CH$_2$CH$_2$N); 4.06 (dd, J(H$_{eq}$-C(5'), H$_{ax}$-C(5')) = 11.0, J(H$_{eq}$-C(5'), H—C(4')) = 6.0, H$_{eq}$-C(5')); 4.12 (t, J(H$_{ax}$-C(5'), H$_{eq}$-C(5')) = J(H$_{ax}$-C(5'), H—C(4')) = 11.0, H$_{ax}$-C(5')); 5.39 (dd, J(H—C(2'), H—C(1')) = 9.5, J(H—C(2'), H—C(3')) = 2.9 H—C(2')); 5.46 (ddd, J(H—C(4'), H$_{ax}$-C(5')) = 11.0, J(H—C(4'), H$_{eq}$-C(5')) = 6.0, J(H—C(4'), H—C(3')) = 2.9, H—C(4')); 6.26 (ψt, J ≈ 2.6, H—C(3')); 6.36 (d, J(H—C(1'), H—C(2')) = 9.5, H—C(1')); 7.24–7.40, 7.44–7.56, 7.61–7.66, 7.72–7.80, 7.84–7.90, 8.06–8.13 (6 m, 16H, 3 Ph, H—C(6)); 7.70, 7.82 (2 m$_c$, 4H, NPht); 8.37 (s, H—N(3)). |
| $^{13}$C-NMR (75 MHz, CDCl$_3$): | 21.19 (CH$_2$CH$_2$N); 36.33 (CH$_2$CH$_2$N); 64.07 (C(5')); 66.81, 68.22 (C(4'), C(2')); 69.29 (C(3')); 78.59 (C(1')); 112.42 (C(5)); 123.31, 132.05, 133.89 (6C, Pht); 128.33, 128.47, 128.47, 128.83, 128,86, 129.31, 129.83, 129.83, 129.94, 133.55, 133.62, 133.69 (18C, 3 Ph); 135.87 (C(6)); 150.39, 162.78 (C(4)); 164.64, 165.01, 165.41 (3C, O$_2$CPh); 168.43 (2C, CO—Pht). |
| MS (ESI$^+$): | 730.2 [M + H]. |

Anal.: calc. for C$_{40}$H$_{31}$N$_3$O$_{11}$ (729.70): C, 65.84, H, 4.28, N, 5.76; found: C, 65.63, H, 4.46, N, 5.53.

5-(2-Phtalimidoethyl)-1-(β-D-ribopyranosyl)uracil (35)

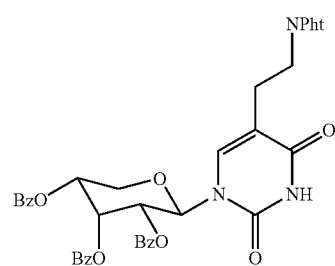

34

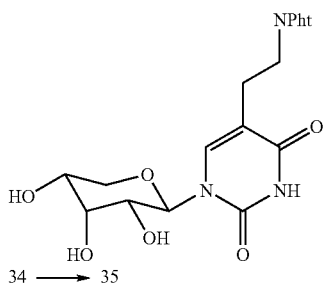

34 → 35

1. Procedure 15 g (20 mmol) of 34 were dissolved in 500 ml of MeOH in a 1 l round-bottomed flask, treated with 324 mg (6 mmol) of NaOMe and stirred at room-temp. overnight with exclusion of water (TLC checking, AcOEt/n-heptane 1:1). Amberlite IR-120 was added to the resulting suspension until the pH was <7. The solid was dissolved in the presence of heat, filtered off hot from the ion exchanger and washed with MeOH. After removing the solvent, the residue was co-evaporated twice using 150 ml of water each time. This yielded 9 g of crude product, which was heated under reflux in 90 ml of MeOH for 10 min. After cooling to room temp., the mixture was treated with 60 ml of Et$_2$O and stored overnight at 4° C. Filtration, washing with Et$_2$O and drying in an oil pump vacuum yielded 7.8 g (93%) of 35.

2. Analytical Data 5-(2-Phtalimidoethyl)-1-(β-D-ribopyranosyl)uracil (35)

| | |
|---|---|
| M.p. | 137° C. (sintering) |
| TLC: | CHCl$_3$/MeOH 5:1, R$_f$ 0.21. |
| UV (MeOH): | λ$_{max}$ 263.0 (8575): λ 299.0 (sh., 1545). |
| IR (KBr): | 3458s, 1772w, 1706s, 1400m, 1364m, 1304m, 1045m. |
| $^1$H-NMR (300 MHz, d$_6$-DMSO + 2 Tr. D$_2$O: | 2.55 (m$_c$, 2H, CH$_2$CH$_2$N); 3.28–3.61 (m, 4H, H—C(2'), H—C(4'), H$_{eq}$-C(5'), H$_{ax}$-C(5')); 3.73 (m$_c$, 2H, CH$_2$CH$_2$N); 3.93 (m, H—C(3')); 5.50 (d, J(H—C(1'), H—C(2')) = 9.3, H—C(1')); 7.41 (s, H—C(6)); 7.84 (s, 4H, NPht). |
| $^{13}$C-NMR (75 MHz, d$_6$-DMSO): | 25.63 (CH$_2$CH$_2$N); 36.62 (CH$_2$CH$_2$N); 64.95 (C(5')); 66.29 (C(4')); 67.37 (C(2')); 71.12 (C(3')); 79.34 (C(1')); 110.39 (C(5)); 122.85, 131.54, 134.08 (6C, Pht); 137.92 (C(6)); 150.84 (C(2)); 163.18 (C(4)); 167.74 (2C, CO—Pht). |
| MS (ESI$^-$): | 416.1 [M − H]. |

1-(2'-O-Benzoyl-β-D-ribopyranosyl)-5-(2-phtalimidoethyl)uracil 10.6 g (0.025 mmol) of 5-(2-phtalimidoethyl)-1-(β-D-ribopyranosyl)uracil were dissolved in 20 ml of pyridine in a heated and argon-flushed 1 l four-necked flask and mixed with 200 ml of dichloromethane. The mixture was cooled to −70° C., 3.82 ml (0.033 mmol) of benzoyl chloride in 5 ml of pyridine and 20 ml of dichloromethane were slowly added dropwise with cooling and the mixture was stirred at −70° C. for 35 min. The reaction mixture was poured onto 600 ml of cooled ammonium chloride solution and the aqueous phase was extracted with ethyl acetate. The combined organic phases were washed with water, dried and concentrated to dryness in vacuo. Chromatography on silica gel (ethyl acetate/heptane 1:1) yielded 7.9 g (60%) of 1-(2'-O-benzoyl-β-D-ribopyranosyl)-5-(2-phtalimidoethyl) uracil.

TLC: R$_f$ 0.24 (ethyl acetate/heptane 4:1)

$^1$H-NMR (300 Mhz, d$_6$-DMSO) 2.67 (m$_e$, 2H, CH$_2$CH$_2$N); 3.66–3.98 (m, 5H, H—C(4'), H$_{eq}$—C(5'), H$_{ax}$—C(5'), CH$_2$CH$_2$N) 4.51 (t, 1H, H—C(3')); 4.98 (dd, 1H, H—C (2')); 6.12 (d, 1H, H—C(1')); 7.19 (s, 1H, H—C(6)); 7.29–7.92 (m, 9H, OBz, NPht).

1-(2-O-Benzoyl-4-O-(4,4'-dimethoxytrityl)-β-D-ribopyranosyl)-5-(2-phtalimidoethyl)uracil 5.6 g (10.73 mmol) of 1-(2-O-benzoyl-β-D-ribopyranosyl-5-(2-phtalimidoethyl)uracil were dissolved in 60 ml of dichloromethane, treated with 4.72 g (13.95 mmol) of 4,4'-dimethoxytrityl chloride and 2.4 ml (13.95 mmol) of N-ethyldiisopropylamine and stirred at RT for 20 min. The reaction mixture was diluted with 100 ml of dichloromethane, washed with sodium hydrogencarbonate solution and 20% citric acid solution, dried and concentrated to dryness in vacuo. Chromatography on silica gel (ethyl acetate/heptane 1:1+2% triethylamine) yielded 7.7 g (87%) of 1-(2-O-benzoyl-4-O-(4,4'-dimethoxytrityl)-β-ribopyransoyl)-5-(2-phtalimidoethyl)uracil.

TLC: R$_f$ 0.53 (ethyl acetate/heptane 1:1+2% triethylamine).

$^1$H-NMR (300 MHz, CDCl$_3$): 2.64 (m$_c$, 2H, CH$_2$CH$_2$N) ; 3.12 (m$_c$, 1H, H—C(4')); 3.59–3.63 and 3.72–3.92 (m, 5H, H—C(3'), H$_{eq}$—C(5'), H$_{ax}$—C(5'), CH$_2$CH$_2$N); 3.81 and 3.82 (s, 6H, CH$_3$O); 4.70 (dd, 1H, H—C(2')); 6.09 (d, 1H, H—C(1')), 7.05 (s, 1H, H—C(6)); 6.84–7.90 (m, 22H, ODmt, OBz, NPht).

1-(3-O-Benzoyl-4-O-(4,4'-dimethoxytrityl)-β-D-ribopyranosyl)-5-(2-phtalimidoethyl)uracil 3 g (3.63 mmol) of 1-(2-O-Benzoyl-4-O-(4,4'-dimethoxytrityl)-β-D-ribopyranosyl)-5-(2-phtalimidoethyl)uracil, 1 g (7.26 mmol) of 4-nitrophenol, 0.44 g (3.63 mmol) of 4-(dimethylamino)pyridine and 3.75 ml (21.78 mmol) of N-ethyldiisopropylamine were dissolved in 5.6 ml of isopropanol and 25 ml of pyridine, heated to 65° C. and stirred at 65° C. for 3 days. The solution was concentrated to dryness in vacuo and the residue was dissolved in 150 ml of dichloromethane. After washing with 20% citric acid solution and sodium hydrogencarbonate solution, the solution was dried over magnesium sulphate. Chromatography on silica gel (ethyl acetate/dichloromethane/isohexane 2:1:1) yielded 2.27 g (76%) of 1-(3-O-benzoyl-4-O-(4,4'-dimethoxytrityl)-β-D-ribopyranosyl)-5-(2-phtalimidoethyl)uracil.

TLC: $R_f$ 0.27 (ethyl acetate/isohexane 2:1+1% triethylamine).

$^1$H-NMR (300 MHz, CDCl$_3$): 2.39 (m$_c$, 2H, CH$_2$CH$_2$N); 2.53 (m$_c$, 1H, H$_{eq}$—C(5')); 3.30 (dd, 1H, H—C(2')); 3.55 (m$_c$, 1H, H$_{ax}$—C(5')); 3.69 (m$_c$, 2H, CH$_2$CH$_2$N); 3.78 and 3.79 (s, 6H, CH$_3$O); 3.79–3.87 (m, 1H, H—C (4')); 5.74 (d, 1H, H—C(1')); 5.77 (m$_c$, 1H, H—C(3')); 6.92 (s, 1H, H—C(6)); 6.74–8.20 (m, 22H, ODmt, OBz, NPht).

1-{2'-O-[(Allyloxy)(diisopropylamino)phosphino]-3'O-benzoyl-4'-O-[(4,4'-dimethoxytriphenyl)methyl]-β-D-ribopyranosyl}-5-(2-phtalimidoethyl)uracil 88 mg (0.11 mmol) of 1-(3-O-benzoyl-4-O-(4,4'-dimethoxytrityl)-β-D-ribopyranosyl)-5-(2-phtalimidoethyl)uracil were dissolved in 5 ml of dichloromethane, treated with 75 µl (0.44 mmol) of N-ethyldiisopropylamine and 70 µl (0.3 mmol) of allyloxychloro(diisopropylamino)phosphine and stirred for 3 h at room temperature. After addition of a further 35 µl (0.15 mmol) of allyloxychloro(diisopropylamino)phosphine to complete the reaction, it was stirred for a further 1 h at room temperature and the reaction mixture was concentrated in vacuo. Chromatography on silica gel (ethyl acetate/heptane: gradient 1:2 to 1:1 to 2:1, in each case with 2% triethylamine) yielded 85 mg (76%) of 1-{2'-O-[(allyloxy)(diisopropylamino)phosphino]-3'O-benzoyl-4'-O-[(4,4'-dimethoxytriphenyl)methyl]-β-D-ribopyranosyl}-5-(2-phtalimidoethyl)uracil.

TLC: $R_f$ 0.36 (ethyl acetate/heptane 2:1).

$^1$H-NMR (,CDCl$_3$, 300 MHz,): selected characteristic positions: 2.28, 2.52 (2 dd, J=5.0, 11.0 Hz, 2H, 2H-5'), 3.79, 3.78 (app. 2 s, 12H, OMe), 6.14 (1 bs, 1H, H-3').

$^{31}$P-NMR (CDCl$_3$): 149.8, 150.6

5.2 Indole-based Linker

N-phthaloyltryptamine is obtained from phthalic anhydride and tryptamine as described (Kuehne et al J. Org. Chem. 43, 13, 1978, 2733–2735). This is reduced with borane-THF to give the indoline (analogously to A. Giannis, et al., Angew. Chem. 1989, 101, 220).

The 3-substituted indoline is first reacted with ribose to give the nucleoside triol and then with acetic anhydride to give the triacetate. The mixture is oxidized with 2,3-dichloro-5,6-dicyanoparaquinone and the acetates are cleaved with sodium methoxide, benzoylated selectively in the 2'-position, DM-tritylated selectively in the 4'-position, and the migration reaction is carried out to give the 3'-benzoate. The formation of the phosphoramidite is carried out in the customary manner. This can be employed for the automated oligbnucleotide synthesis without alteration of the synthesis protocols.

Procedure

3-(N-Phthaloyl-2-aminoethyl)indoline

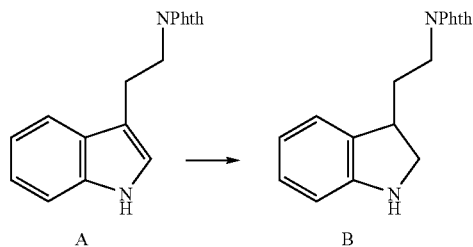

51.4 g (177 mmol) of phthaloyltryptamine A were dissolved in 354 ml of 1M borane-THF solution (2 eq.) under a nitrogen atmosphere and cooled to 0° C. 354 ml of trifluoroacetic acid were slowly added dropwise at 0° C. (caution: evolution of gas) and the mixture was stirred for 30 min. (TLC checking: EtOAc). 17.3 ml of water were then added, and the mixture was stirred for 10 min and concentrated in vacuo. The residue was dissolved in 10% strength NaOH solution/dichloromethane, and the organic phase was separated off, dried over NaSO$_4$, filtered and concentrated in vacuo. The residue [50.9 g] was recrystallized from hot ethanol (3 l). 41.4 g of B were obtained, m.p. 161–162° C. The mother liquor was concentrated in vacuo and the residue was again recrystallized from ethanol. A further 3.2 g of B were obtained, m.p. 158–159° C.

Total yield: 44.6 g (153 mmol) of B, i.e. 86%.

$^1$H-NMR (CDCl$_3$, 300 MHz): 1.85–2.00, 2.14–2.28 (2 m, 2×1H, CH$_2$CH$_2$NPhth); 2.70 (bs, 1H, NH), 3.24–3.38, 3.66–3.86 (2 m, 5H, CH$_2$CH$_2$NPhth, H-2a, H-2b, H-3), 6.62 (d, J=8.0 Hz, 1H, H-7), 6.66–6.72 (m, 1H, H-5), 6.99 (app t, J=7.5 Hz, 1H, H-6), 7.14 (d, J=8.0 Hz, 1H, H-4), 7.64–7.74, 7.78–7.86 (2 m, 2×2H, Phth).

$^{13}$C-NMR (CDCl$_3$, 75 MHz): 32.70, 36.10 (2 t, C-2, CH$_2$CH$_2$NPhth), 39.62 (d, C-3), 53.04 (t, CH$_2$NPhth), 109.65 (d, C-7), 118.74 (d, C-5), 123.25 (d, Phth), 123.92, 127.72 (2 d, C-4, C-6), 131.81 (s, C-3a), 132.14 (s, Phth), 133.99 (d, Phth), 151.26 (s, C-7a), 168.38 (s, C=O).

Calc.: C: 73.96, H: 5.52, N: 9.58; found: C: 73.89, H: 5.57, N: 9.55.

MS (ES$^+$): 293 (MH$^+$, 100%)

3-(N-Phthaloyl-2-aminoethyl)-1-(2',3',4'-tri-O-acetyl-β-D-ribopyranosyl)indole

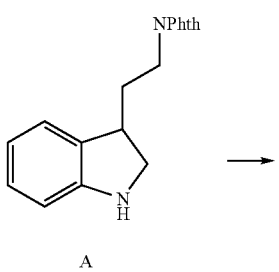

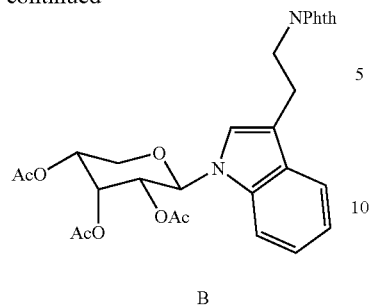

B 45.2 g (155 mmol) of A and 23.2 g (155 mmol; 1.0 eq.) of D-ribose were suspended in 750 ml of dry ethanol and heated to reflux for 4 h under a nitrogen atmosphere (TLC checking: CH$_2$Cl$_2$/MeOH 10:1). After cooling to RT, the mixture was concentrated in vacuo. The residue was dissolved in 300 ml of pyridine and treated with 155 ml of acetic anhydride with ice-cooling. After 15 min., the ice bath was removed and the mixture was stirred at RT for 18 h (TLC checking: EtOAc/isohexane 1:1). This solution was concentrated in vacuo and co-evaporated three times with 300 ml of toluene each time. The oil obtained was dissolved in 900 ml of dichloromethane and treated with 38.8 g (171 mmol; 1.1 eq.) of 2,3-dichloro-5,6-dicyanoparaquinone with ice-cooling. After 15 min., the ice bath was removed and the mixture was stirred at RT for 1.5 h (TLC checking: EtOAc/isohexane 1:1). The deposited precipitate was filtered off with suction and washed with dichloromethane and discarded. The filtrate was washed with 600 ml of satd. NaHCO$_3$ solution. The precipitate deposited in the course of this was again filtered off with suction and washed with dichloromethane and discarded. The combined organic extracts were dried over Na$_2$SO$_4$ and concentrated in vacuo. The residue (90.9 g) was purified by flash chromatography on silica gel 60 (10×25 cm; EtOAc/isohexane 2:3).

The following were obtained: 21.5 g of pure B and 46.83 g of mixed fractions, which after fresh chromatography yielded a further 20.4 g of pure B.

Total yield: 41.9 g (76 mmol) of B, i.e. 49%.

$^1$H-NMR (CDCl$_3$, 300 MHz): 1.64, 1.98, 2.19 (3 s, 3×3H, Ac), 3.06 (t, J=8.0 Hz, 2H, CH$_2$CH$_2$NPhth), 3.81–4.00 (m, 4H, H-5'ax, H-5'eq, CH$_2$NPhth), 5.13 (ddd, J=2.5, 6.0, 10.5 Hz, 1H, H-4'), 5.36(dd, J=3.5, 9.5 Hz, 1H, H-2'), 5.71(d, J=9.5 Hz, 1H, H-1'), 5.74(app t, J=3.0 Hz, 1H, H-3'), 7.02(s, 1H, H-2), 7.04–7.10, 7.13–7.19 (2 m, 2×1H, H-5, H-6), 7.33 (d, J=8.0 Hz, 1H, H-7), 7.58–7.66, 7.72–7.80(2 m, 5H, Phth, H-4).

$^{13}$C-NMR (CDCl$_3$, 75 MHz): 20.23, 20.65, 20.87 (3 q, Ac), 24.41, 38.28 (2 t, CH$_2$CH$_2$), 63.53 (t, C-5'), 66.24, 68.00, 68.64 (3 d, C-2', C-3', C-4'), 80.33 (d, C-1'), 109.79 (d, C-7), 113.95 (s, C-3), 119.33, 120.39, 122.04, 122.47 (4 d, C-4, C-5, C-6, C-7), 123.18 (d, Phth), 128.70, 132.17 (2 s, C-3a, Phth), 133.87 (d, Phth), 136.78 (s, C-7a), 168.243, 168.77, 169.44, 169.87 (4 s, C=O).

Calc.: C: 63.50, H: 5.15, N: 5.11; found: C: 63.48, H: 5.16, N: 5.05.

MS (ES$^+$): 566 (M+NH$_4^+$, 82%), 549 (MH$^+$, 74%), 114 (100%).

3-(N-Phthaloyl-2-aminoethyl)-1-β-D-ribo-pyranosyl-indol

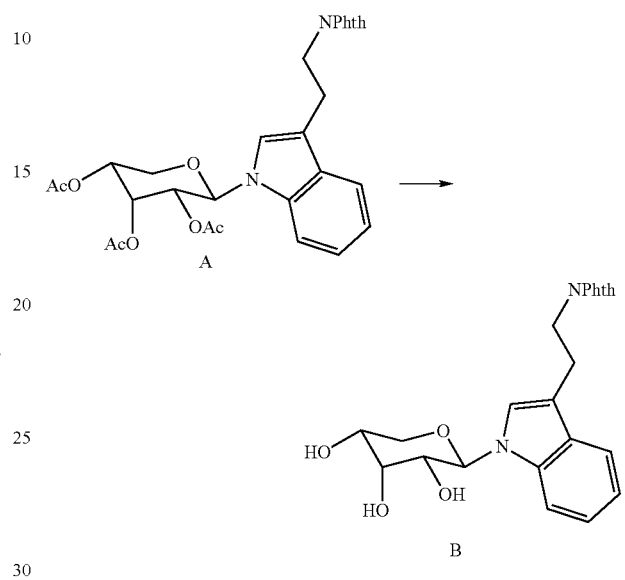

44.1 g (80 mmol) of A were dissolved in 400 ml of anhydrous methanol under a nitrogen atmosphere. The mixture was treated with 4.0 ml of 30% strength sodium methoxide solution with ice-cooling and then stirred for 18 h at RT. The deposited precipitate was filtered off with suction and washed with cold ethanol. The filtrate was concentrated in vacuo. The residue was taken up in dichloromethane. This solution was washed with satd. NaHCO$_3$ solution, dried over Na$_2$SO$_4$ and concentrated in vacuo. The residue obtained was recrystallized from hot ethanol together with the precipitate deposited from the reaction solution. 22.6 g of B were obtained, m.p. 196–198° C. The mother liquor was concentrated in vacuo and the residue was again recrystallized from ethanol. A further 9.2 g of B were obtained, m.p. 188–194° C.

Total yield: 25.8 g of B, i.e. 76%.

$^1$H=NMR (MeOD, 300 MHz): 3.09 (app. t, J=7.0 Hz, 2H, CH$_2$CH$_2$NPhth), 3.64–3.98 (m, 5H, H-4', H-5'ax, H-5'eq, CH$_2$NPhth), 4.05 (dd, J=3.5, 9.5 Hz, 1H, H-2'), 4.22 (app t, J=3.0 Hz, 1H, H-3'), 5.65 (d, J=9.5 Hz, 1H, H-1'), 6.95–7.05, 7.09–7.16 (2 m, 2×1H, H-5, H-6), 7.25 (s, 1H, H-2), 7.44 (d, J=8.0 Hz, 1H, H-7), 7.60 (d, J=8.0 Hz, 1H, H-4), 7.74–7.84 (m, 4H, Phth).

$^{13}$C-NMR (d$_6$-DMSO, 75 MHz): 23.87, 37.79 (2 t, CH$_2$CH$_2$NPhth), 64.82 (t, C-5'), 66.74 (d, C-4'), 68.41 (d, C-2'), 71.42 (d, C-3'), 81.37 (d, C-1'), 110.42 (d, C-7), 111.05 (s, C-3), 118.17, 119.21, 121.36, 122.92, 123.80 (5 d, C-2, C-4, C-5, C-6, NPhth), 127.86, 131.59 (2 s, C-3a, Phth), 134.27 (d, Phth), 136.62 (s, C-7a), 167.72 (s, C=O).

MS(ES$^-$): 457 (M+OH$^-$+H$_2$O, 49%), 439 (M+OH$^-$, 100%), 421 (M−H$^+$, 28%)

35
1-(2'-O-Benzoyl-β-D-ribopyranosyl)-3-(N-phthaloyl-2-aminoethyl)indole

36
1-{3'-O-Benzoyl-4'O-[(4,4'-dimethoxytriphenyl)methyl-β-D-ribopyranosyl}-3-(N-phthaloyl-2-aminoethyl)indole

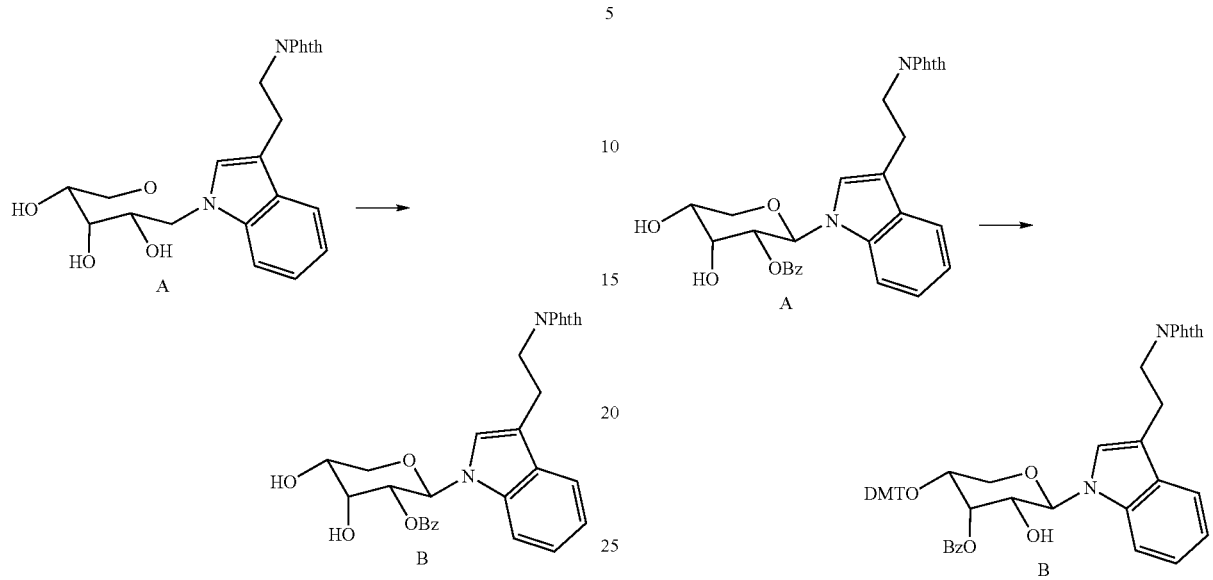

10.6 g (25 mmol) of A was taken up in 250 ml of dry dichloromethane under a nitrogen atmosphere. The mixture was treated with 305 mg of DMAP (2.5 mmol) and 20 ml of pyridine. It was heated until everything was in solution and then cooled to −78° C. 3.35 ml of benzoyl chloride (28.8 mmol) dissolved in 8 ml of dichloromethane were now added dropwise in the course of 15 min. TLC checking (EtOAc/hexane 3:1) after a further 30 min indicated complete reaction. After 45 min, the cold solution was added directly to 200 ml of satd. $NH_4Cl$ solution through a folded filter and the filter residue was washed with dichloromethane. The organic phase was washed once with water, dried over $MgSO_4$ and concentrated. The residue was coevaporated twice with toluene and purified by flash chromatography on 10×20 cm silica gel using EtOAc/hexane 3:1. 8.1 g of B (64%) were obtained.

$^1$H-NMR ($CDCl_3$, 300 MHz): 2.45, 2.70 (2 bs, 2×1H, OH), 3.04 (t, J=8.0 Hz, 2H, C$\underline{H}_2$CH$_2$NPhth), 3.80–4.20 (m, 5H, H-4', H-5'ax, H-5'eq, C$\underline{H}_2$NPhth), 4.63 (bs, 1H, H-3'), 5.46 (dd, J=3.5, 9.5 Hz, 1H, H-2'), 6.03 (d, J=9.5 Hz, 1H, H-1'), 7.08–7.31 (m, 5H, H-2, H-5, H-6, Bz-m-H), 7.41–7.48 (m, 1H, H-Bz-p-H), 7.50 (d, J=8.0 Hz, 1H, H-7), 7.64–7.79 (m, 7H, Phth, H-4, Bz-o-H).

$^{13}$C-NMR ($d_6$-DMSO, 75 MHz): 24.40, 38.22 (2 t, $\underline{C}H_2$ $\underline{C}H_2$NPhth), 65.95 (t, C-5'), 66.65 (d, C-4'), 69.55 (d, C-3'), 71.87 (d, C-2'), 79.57 (d, C-1'), 109.96 (d, C-7), 113.70 (s, C-3), 119.21, 120.21, 122.11, 122.41, 123.14, (5 d, C-2, C-4, C-5, C-6, NPhth), 128.28 (d, Bz), 128.58, 128.59, (2 s, C-3a, Bz), 129.62 (d, Phth), 132.05 (s, Phth), 133.81 (Bz), 136.97 (s, C-7a), 165.12, 168.29 (2 s, C=O).

MS (ES$^-$): 525 (M−H$^+$, 12%), 421 (M-PhCO$^+$, 23%), 107 (100%).

8.9 g (16.9 mmol) of A was suspended in 135 ml of dry dichloromethane under a nitrogen atmosphere. The mixture was treated with 206 mg of DMAP (1.68 mmol), 5.8 ml of N-ethyldiisopropylamine (33.7 mmol) and about 12 ml of pyridine (until solution was complete). It was now treated with 34 g of molecular sieve 4 Å and stirred for 30 min. After cooling to 0° C., it was treated with 11.4 g of DMTCl (33.7 mmol) and stirred for 75 min after removing the cooling bath. A further 1.94 g (0.34 eq) and, after a further 40 min, 1.14 g (0.2 eq) and, after a further 65 min, 1.14 g of DMTCl (0.2 eq) were then added. After 4.25 h the reaction was complete. The mixture was then treated with 25.3 ml of n-propanol (20 eq), stirred for a further 30 min and then concentrated cautiously (foam formation). The residue was dissolved in 100 ml of pyridine. It was treated with 1.85 g of DMAP (15.1 mmol; 0.9 eq), 13.05 ml of N-ethyldiisopropylamine (101 mmol; 6.0 eq), 71 ml of n-propanol (940 mmol; 56 eq) and 3.74 g of p-nitrophenol (26.9 mmol; 1.6 eq). This mixture was stirred under nitrogen for 96 h at 75–80° C. After cooling to room temperature, the mixture was filtered through Celite and concentrated. The residue was purified by flash chromatography on 9×17 cm silica gel using toluene/diethyl ether/triethylamine 90:10:1. The product-containing fractions (9.25 g) were first recrystallized from EtOAc and then reprecipitated from toluene/methanol. 5.86 g of B (42%) were obtained.

$^1$H-NMR ($CDCl_3$, 300 MHz): 2.64 (bs, 1H, OH), 2.68 (dd, J=5.0, 11.5 Hz, 1H, H-5'eq), 2.94 (dd, J=7.5, 16.0 Hz, 1H, C$\underline{H}_2$CH$_2$NPhth), 3.03 (dd, J=8.0, 16.0 Hz, 1H, C $\underline{H}_2$CH$_2$NPhth), 3.67–3.74 (m, 1H, H-5'ax), 3.69, 3.70 (2 s, 2×3H, OMe), 3.85 (t, J=7.5 Hz, 2H, CH$_2$C$\underline{H}_2$NPhth), 3.94 (ddd, J=3.0, 5.0, 10.5 Hz, 1H, H-4'), 4.03 (dd, J=3.5, 9.0 Hz, 1H, H-2'), 5.51 (d, J=9.0 Hz, 1H, H-1'), 5.86 (bs, 1H, H-3'), 6.68–7.66 (m, 25H), 8.19–8.30 (m, 2H).

$^{13}$C-NMR ($CDCl_3$, 75 MHz): 24.16, 38.80 (2 t, $\underline{C}H_2$ $\underline{C}H_2$NPhth), 55.25, 55.26 (2 q, Ome), 65.58 (t, C-5'), 68.29, 69.19, 73.83 (3 d, C-2', C-3', C-4'), 83.03 (d, C-1'), 87.31 (CAr₃)110.03 (d, C-7), 113.37, 113.47 (2 d), 113.53 (s, C-3), 118.95, 120.20, 122.28, 122.31, 123.10, 127.07, 128.02, 128.08, 128.68 (9 d), 128.74 (s), 130.02, 130.19, 130.22 (3 d), 130.37, 131.95 (2 s), 133.40, 133.83 (2 d), 135.98, 136.14, 136.56, 145.12, 158.82, 166.76, 168.52 (7 s, C-7a, 2 COMe, 2 C=O).

1-{2'O-(Allyloxy)(diisopropylamino)phosphino)-3'-O-benzoyl-4'O-[(4,4'-dimethoxytriphenyl)methyl]-β-D-ribopyranosyl}-3-(N-phthaloyl-2-aminoethyl) indole (2 diastereomers)

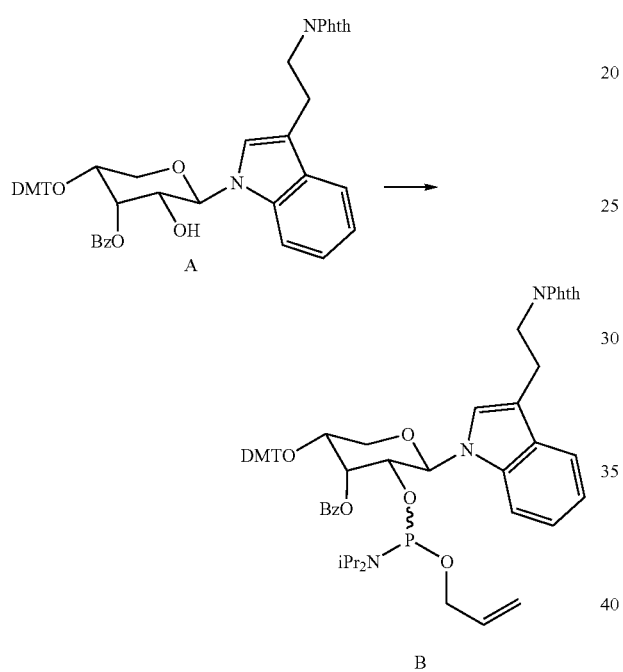

1658 mg of alcohol A (2.0 mmol) was dissolved in 10 ml of dry dichloromethane under an argon atmosphere. The solution was treated with 1.03 ml of N-ethyldiisopropylamine (6.0 mmol) and 0.63 ml of monoallyl n-diisopropylchlborphosphoramidite (2.8 mmol) and stirred for 1 h at room temperature. The excess phosphorylation reagent was then destroyed by addition of 61 μl (0.8 mmol) of isopropanol. After 10 min, the mixture was concentrated in vacuo and the residue was purified by flash chromatography on 3.3×21 cm silica gel using hexane/EtOAc/NEt₃ (75:25:1). The product-containing fractions were concentrated, taken up in CCl₄ and concentrated again. 2.04 g of an almost colourless foam (quant.) were obtained, which can be used thus directly for oligomerization and can be kept at −20° C. for a number of weeks.

TLC on silica gel (EtOAc/hexane/NEt₃ 33:66:1): 0.41

$^1$H-NMR (CDCl₃, 300 MHz): selected characteristic positions: 2.42, 2.53, (2 dd, J=5.0, 11.0 Hz, 2H, 2 H-5'eq), 3.76, 3.77, 3.78, 3.79 (4 s, 4×3H, OMe), 5.70, 5.73 (2 d, J=9.0 Hz, 2H, 2H-1'), 6.16, 6.29 (2 bs, 2H, 2 H-3')

$^{31}$P-NMR (CDCl₃): 150.6, 151.0

5.3 Lysine-based Linker

The synthesis is depicted in Scheme 7 and is described in detail below.

Scheme 7:
Synthesis of the lysine linker

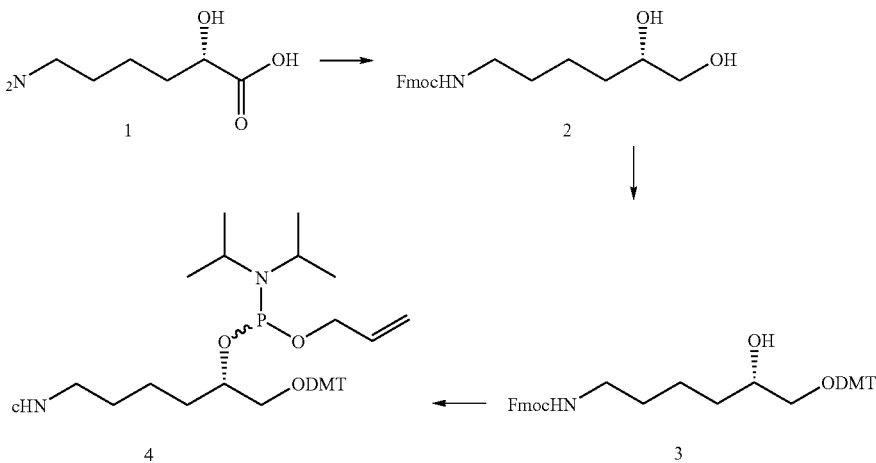

6-Amino-2(S)-hydroxyhexanoic acid (1) was prepared from L-lysine in a manner known from the literature by diazotization and subsequent hydrolysis (K.-I. Aketa, Chem. Pharm Bull. 1976, 24, 621).

2-(S)-N-Fmoc-6-amino-1,2-hexanediol (2)

3.4 g of LiBH$_4$ (156 mmol, 4 eq) are dissolved under argon in 100 ml of abs. THF (exothermic!). After cooling to about 30° C., 39.6 ml of TMSCl (312 mmol, 8 eq) are slowly added dropwise (evolution of gas!), a precipitate being formed. 5.74 g of 6-amino-2(S)-hydroxyhexanoic acid (1) (39 mmol) are added in portions in an argon countercurrent and the mixture is heated to 65° C. until the TLC (silica gel; i-PrOH/conc. NH$_4$OH/water 7:2:1; staining with ninhydrin) no longer shows any starting material (about 3 h). The mixture is cautiously treated with 120 ml of methanol with ice-cooling (strong evolution of gas!). The solvent is concentrated in vacuo, and the residue is co-evaporated three times with 200 ml of methanol each time and then dissolved in 100 ml of abs. DMF. After addition of 16 ml of ethyldiisopropylamine (93.6 mmol, 2.4 eq), the mixture is cooled to 0° C. and treated; in portions with 12.1 g of FmocCl (46.8 mmol, 1.2 eq) After 15 minutes, the cooling bath is removed and the mixture is stirred at room temperature until the starting: material has been consumed (about 3 h; TLC checking: silica gel; CHCl$_3$/MeOH/HOAc/water 060:30:3: 5) The reaction solution is added to 600 ml of satd. NaHCO$_3$ solution. The precipitate is filtered off, washed with 200 ml of water and dried at 50° C. in high vacuum until the weight is constant (about 6 h). 13.9 g of a colourless solid is obtained, which is recrystallized from ethyl acetate (40 ml)/n-hexane (35 ml). Yield: 9.05 g (65%).

$^1$H-NMR (300 MHz, CDCl$_3$): 7.68, 7.51 (2 d, J=8.0 Hz, in each case 2H, Ar—H), 7.32 (t, J=8.0 Hz, 2H, Ar—H), 7.23 (dt, J=1.6, 8.0 Hz, 2H, Ar—H), 4.92 (bs, 1H, NH), 4.32 (d, J=7 Hz, 2H, OCOCH$_2$), 4.13 (bt, J=7.0 Hz, OCOCH$_2$CH), 3.64–3.58 (m, 1H, H-1, H-1', H-2, H-6, H-6'), 3.54 (dd, J=3.2, 11.0 Hz, 1H, H-1, H-1', H-2, H-6, H-6'), 3.35 (dd, J=7.4, 11.0 Hz, 1H, H-1, H-1', H-2, H-6, H-6'), 3.16–3.06 (m, 2 H H-1, H-1', H-2, H-6, H-6'), 3.0–2.0 (bs, 2H, OH), 1.52–1.18 (m, 6H, H-3, H-3', H-4, H-4', H-5, H-5').

2-(S)-N-Fmoc-O$^1$-DMT-6-amino-1,2-hexanediol (3) was DM-tritylated according to WO 89/02439

2-(S)-N-Fmoc-O$^1$-DMT-O$^2$-allyloxydiisopropylaminophosphinyl-6-amino-1,2-hexanediol (4)

0.51 ml of ethyldiisopropylamine (3.0 mmol, 3 eq) and 0.33 ml of chloro-N,N-diisopropylaminoallyloxyphosphine (1.5 mmol, 1.5 eq) are added under argon to a solution of 670 mg of the alcohol (3) (1.02 mmol) in 10 ml of abs. dichloromethane. The mixture is stirred at room temperature for 2 h, the solvent is stripped off in vacuo and the residue obtained 1 is purified by flash chromatography on 3.2×16 cm silica gel (EtOAc/isohexane/NEt$_3$ 20:80:1). 839 mg (97%) of a slightly yellowish oil are obtained.
TLC: silica gel; EtOAc/isohexane/NEt$_3$ 50:50:1; UV; R$_f$=0.77.
$^1$H=NMR (300 MHz, CDCl$_3$): 7.70–6.68 (m, 21H, Ar—H), 4.92–4.62 (m, 1H, NH), 4.31 (d, J=7.0 Hz, H, OCOCH$_2$), 4.13 (t, J=7.0 Hz, 1H, OCOCH$_2$CH), 3.98–3.40 (m, 5H), 3.77 (2 s, in each case 3H, OMe), 3.16–2.86 (m, 4H), 2.58 (t, J=7.0 Hz, 1H, CHCN), 2.38 (t, 1H, CHCN), 1.80–1.20 (m, 6 H), 1.20, 1.18, 1.17, 1.16, 1.15, 1.13, 1.08, 1.06 (8 s, 12H, NMe).
$^{31}$P-NMR (300 MHz, CDCl$_3$): 149.5, 149.0 (2 s)

Example 6

Synthesis of a p-RNA Oligo of the Sequence 4'-Indole Linker-A8-2' Using Benzimidazolium Triflate as a Coupling Reagent 108 mg of indole linker phosphoramidite and 244 mg of sphoramidite; are weighed into a synthesizer vial and left in a high vacuum for 3 h in a desiccator over KOH together with the column packed with 28.1 mg of CDP support, loaded with A unit. The phosphoramidites are dissolved 1 ml (indole linker) or 2.5 ml (A phosphoramidite) of acetonitrile and a few beads of the molecular sieve are added and left closed in a desiccator over KOH.

200 mg of iodine are dissolved in 50 ml of acetonitrile with vigorous stirring. After everything has dissolved (visual control), 23 ml of water and 4.6 ml of symcollidine are added and the solution is thoroughly mixed once. For detritylation, a 6% strength solution of dichloroacetic acid in dichloromethane is employed. The capping reagent (acetic anhydride+base) is purchased and used as customary for oligonucleotide synthesis.

Benzimidazolium triflate is recrystallized from hot acetonitrle and dried. Using the almost colourless crystals, a 0.1 M solution in anhydrous acetonitrile is prepared as a cuping reagent. During the synthesis, this solution always remains clear and no blockages in the synthesizer tubing occur.

Modified DNA coupling cycling the Eppendorf Ecosyn 300+ (DMT-one):

| Detritylation | 7 minutes |
|---|---|
| Coupling | 1 hour |
| Capping | 1.5 minutes |
| Oxidation | 1 minute |

20 mg of tetrakis(triphenylphosphine)palladium is dissolved in 1.5 ml of dichloromethane, 20 mg of diethylammonium hydrogencarbonate, 20 mg of triphenylphosphine and the glass support carrying the oligonucleotide are added, tightly sealed (parafilm) and the vial is agitated for 5 h at RT. The glass support is then filtered off with suction by means of an analytical suction filter, and washed with dichloromethane, with acetone and with water.

The support is suspended using aqueous 0.1 molar sodium diethyldithiocarbamate solution and left at RT. For 45 min. It is filtered off with suction, and washed with water, acetone, ethanol and dichloromethane. The support is suspended in 1.5 ml of 24% strength hydrazine hydrate solution, shaken for, 24–36 h at 4° C. and diluted to 7 ml with 0.1 molar triethylammonium hydrogencarbonate buffer (TEAB buffer). It was washed until hydrazine-free by means of a Waters Sep-Pak cartridge. It is treated with 5 ml of an 80% strength formic acid solution, and concentrated to dryness after 30 min. The residue is taken up in 10 ml of water, extracted with dichloromethane, and the aqueous phase is concentrated and then HPL chromatographed (tR=33 min, gradient of acetonitrile in 0.1M triethylammonium acetate buffer). Customary desalting (Waters Sep-Pak cartridge) yields the oligonucleotide.

Yield: 17.6 OD

Substance identity proved by ESI mass spectroscopy:
M(calc.)=3082 D, (M+2H)$^{2+}$(found)=1541.9 D.

Example 7

Preparation of Conjugates

1. Sequential Process

A p-RNA oligomer of the sequence $A_8$, i.e. an octamer, is first prepared on the Eppendorf Ecosyn D 300+ as described in Example 2 and the following reagents are then exchanged: 6% strength dichloroacetic acid for 2% strength trichloroacetic acid, iodine in collidine for iodine in pyridine, benzimidazolium triflate solution for tetrazole solution. After changing the synthesis programme, a DNA oligomer of the sequence GATTC is further synthesized according to known methods (M. J. Gait, Oligonucleotide Synthesis, IRL Press, Oxford, UK 1984). The deallylation, hydrazinolysis, HPL chromatography and desalting is carried out as described for the p-RNA oligomer (see above) and yields the desired conjugate.

2. Convergent Process

As described in Example 2, a p-RNA oligomer having the sequence 4'-indole linker-$A_8$-2' is prepared, purified, and iodoacetylated. A DNA oligomer of the sequence GATTC-thiol linker is synthesized according to known methods (M. J. Gait, Oligonucleotide Synthesis, IRL Press, Oxford, UK 1984) and purified (3'-thiol linker from Glen Research: No. 20-2933). On allowing the two fragments to stand (T. Zhu et al., Bioconjug. Chem. 1994, 5, 312) in buffered solution, the conjugate results, which is finally purified by means of HPLC.

Example 8

Conjugation of a Biotin Radical to an Amino-modified p-RNA

First, analogously to the procedure described in Example 6, a p-RNA oligomer of the sequence TAGGCAAT, which is provided with an amino group at the 4'-end by means of the 5'-amino modifier 5 of Eurogentec (2-(2-(4-monomethoxytrityl)aminoethoxy)ethyl 2-cyanoethyl (N,N-diisopropyl) phosphoramidite), was synthesized and worked up. The oligonucleotide (17.4 OD, 0.175 µmol) was taken up in 0.5 ml of basic buffer, 1.14 mg (2.5 µmol) of biotin-N-hydroxysuccinimide ester were dissolved in 114 µl of DMF (abs.) and the solution was allowed to stand at RT for 1 h. The resulting conjugate was purified by means of preparative HPLC and the pure product was desalted using a Sepak.

Yield: 8.6 OD (49%)
M (calc.)=3080 D, M (eff.)=3080.4 D

Example 9

Preparation of Cyanine or Biotin-labelled p-RNA Online

The various A,T,G,C and Ind (Ind=aminoethylindole as a nucleobase) phosphoramidites were first prepared according to known processes. Cyanine (Cy3-CE) and biotin phosphoramidite were obtained from Glen Research.

The fully automatic solid-phase synthesis was carried out using 15 µmol in each case. One synthesis cycle consists of the following steps
(a) Detritylation: 5 minutes with 6% DCA (dichloroacetic acid) in $CH_2Cl_2$ (79 ml);
(b) Washing with $CH_2Cl_2$ (20 ml), acetonitrile (20 ml) and then flushing with argon;
(c) Coupling: washing of the resin with the activator (0.5 M pyridine.HCl in $CH_2Cl_2$, 0.2 ml; 30 minutes' treatment with activator (0.76 ml) and corresponding phosphoramidite (0.76 ml: 8 eq; 0.1 M in acetonitrile) in the ratio 1:1;
(d) Capping: 2 minutes with 50% Cap A (10.5 ml) and 50% Cap B (10.5 ml) from Perseptive (Cap A: THF, lutidine, acetic anhydride; Cap B: 1-methylimidazole, THF, pyridine).
(e) Oxidation: 1 minute with 120 ml of iodine solution (400 mg of iodine in 100 ml of acetonitrile, 46 ml of $H_2O$ and 9.2 ml of sym-collidine).
(f) Washing with acetonitrile (22 ml).

To facilitate the subsequent HPLC purification of the oligonucleotides, the last DMT (dimethoxytrityl) or MMT (monomethoxytrityl) protective group was not removed from biotin or cyanine monomers. The detection of the last coupling with the modified phorphoramidites was carried out after the synthesis with 1% of the resin by means of a trityl cation absorption in UV (503 nm).

Work-up of the Oligonucleotide

The allyl ether protective groups were removed with a solution of tetrakis(triphenylphosphine)palladium (272 mg), triphenylphosphine (272 mg) and diethylammonium hydrogencarbonate in $CH_2Cl_2$ (15 ml) after 5 hours at RT. The glass supports were then washed with $CH_2Cl_2$ (30 ml), acetone (30 ml) and water (30 ml). In order to remove palladium complex residues, the resin was rinsed with an aqueous 0.1 M sodium diethyldithiocarbamate hydrate solution. The abovementioned washing operation was carried out once more in a reverse order. The resin was then dried in a high vacuum for 10 minutes. The removal step from the glass support with simultaneous debenzoylation was carried out in 24% hydrazine hydrate solution (6 ml) at 4° C. After HPLC checking on RP 18 (18–25 hours), the oligonucleotide "Trityl ON" was freed from the hydrazine by means of an activated (acetonitrile, 20 ml) Waters Sep-Pak Cartridge. The hydrazine was washed with TEAB 0.1 M (30 ml). The oligonucleotide was then eluted with acetonitrile/TEAB, 0.1 M (10 ml). The mixture was then purified by means of HPLC (for the separation of fragment sequences) and the DMT deprotection (30 ml of 80% strength aqueous formic acid) was carried out. Final desalting (by means of Sep-Pak Cartridge, with TEAB buffer 0.1 M/acetonitrile: 1/1) yielded the pure cyanine- or biotin-labelled oligomers.

An aliquot of this oligo solution was used for carrying out an ESI-MS.

4' Cy-AIndTTCCTA 2': calculated M=3026, found (M+H)$^+$=3027.

4' Biotin-TAGGAAIndT 2': calculated M=3014, found (M+2H)$^{2+}$ m/e 1508 and (M+H)$^+$ m/e 3015.

The oligos were freeze-dried for storage.

Example 10

Iodoacetylation of p-RNA with N-(iodoacetyloxy)-succinimide p-RNA sequence: 4' AGGCAIndT 2' $M_w$=2266.56 g/mol (Ind=indole-CH$_2$—CH$_2$—NH$_2$-linker)

1 eq. of the p-RNA was dissolved (1 ml per 350 nmol) in a 0.1 molar sodium hydrogencarbonate solution (pH 8.4) and treated (40 µl per mg) with a solution of N-(iodoacetyloxy)succinimide in DMSO. The batch was blacked out with aluminium film and it was allowed to stand at room temperature for 30–90 minutes.

The progress of the reaction was monitored by means of analytical HPLC. The standard conditions are:

Buffer A: 0.1 molar triethylammonium acetate buffer in water

Buffer B: 0.1 molar triethylammonium acetate buffer in water:acetonitrile 1:4

Gradient: starting from 10% B to 50% B in 40 minutes

Column material: 10 µM LiChrosphere® 100 RP-18 from Merck Darmstadt GmbH; 250×4 mm Retention time of the starting materials: 18.4 minutes Retention time of the products in this case: 23.1 minutes After reaction was complete, the batch was diluted to four times the volume with water. A Waters Sep-Pak Cartridge RP-18 (from 15 OD 2 g of packing) was activated with 2×10 ml of acetonitrile and 2×10 ml of water, the oligo was applied and allowed to sink in, and the reaction vessel was washed with 2×10 ml of water, rewashed with 3×10 ml of water in order to remove salt and reagent, and eluted first with 5×1 ml of 50:1 water: acetonitrile and then with 1:1 water:acetonitrile. The product eluted in the 1:1 fractions in very good purity. The fractions were concentrated in the cold and in the dark, combined and concentrated again.

The yields were determined by means of UV absorption spectrometry at 260 nm.

Mass spectrometry:
Sequence: 4' AGGCAInd(CH$_2$CH$_2$NHCOCH$_2$-I)T 2'
calculated mass: 2434.50 g/mol
found mass MH$_2^{2+}$: 1217.9 g/mol=2433 g/mol.

Example 11

Conjugation of p-RNA to a Peptide of the Sequence CYSKVG

The iodoacetylated p-RNA ($M_w$=2434.50 g/mol) was dissolved in a buffer system (1000 µl per 114 nmol) and then treated with a solution of the peptide in buffer (2 mol of CYSKVG peptide; $M_w$=655.773 g/mol; 228 nmol in 20 µl of buffer).

Buffer system: Borax/HCl buffer from Riedel-de Haën, pH 8.0, was mixed in the ratio 1:1 with a 10 millimolar solution of EDTA disodium salt in water and adjusted to pH 6.3 using HCl. A solution was obtained by this means which contained 5 mM Na$_2$EDTA.

The batch was left at room temperature in the dark until conversion was complete. The reaction was monitored by means of HPLC analysis.

The standard conditions are:

Buffer A: 0.1 molar triethylammonium acetate buffer in water

Buffer B: 0.1 molar triethylammonium acetate buffer in water:acetonitrile 1:4

Gradient: starting from 10% B to 50% B in 40 minutes

Column material: 10 µM LiChrosphere® 100 RP-18 from Merck Darmstadt GmbH; 250×4

Retention time of the starting material: 17.6 minutes

Retention time of the product: 15.5 minutes

After reaction was complete the batch was purified directly by means of RP-HPLC.

(Standard conditions see above).

The fractions were concentrated in the cold and in the dark, combined and concentrated again. The residue was taken up in water and desalted. A Waters Sep-Pak Cartridge RP-18 (from 15 D 2 g of packing) was activated with 2×10 ml of acetonitrile and 2×10 ml of water, the oligo was applied and allowed to sink in, and the reaction vessel was washed with 2×10 ml of water, rewashed with 3×10 ml of water in order to remove the salt, and eluted with water: acetonitrile 1:1. The product fractions were concentrated, combined, and concentrated again.

The yields were determined by means of UV absorption spectrometry at 260 nm. They reached 70–95% of theory.

Mass spectrometry:
Sequence: 4' AGGCAInd(CH$_2$CH$_2$NHCOCH$_2$-CYSKVG)T 2'
calculated mass: 2962.36 g/mol
found mass MH$_2^{2+}$: 1482.0 g/mol=2962 g/mol.

Example 12

Conjugation of p-RNA to a Peptide Library

The iodoacetylated p-RNA ($M_w$=2434.50 g/mol was dissolved (1300 µl per 832 nmol) in a buffer system and then treated in buffer (8 mol; mean molecular mass $M_m$=677.82 g/mol; 4.5 mg=6.66 µmol in 200 µl of buffer) with a solution of the peptide library (CKR-XX-OH); X=Arg, Asn, Glu, His, Leu, Lys, Phe, Ser, Trp, Tyr).

Buffer system: Borax/HCl buffer from Riedel-de Haen, pH 8.0, was mixed in the ratio 1:1 with a 10 millimolar solution of EDTA disodium salt in water and adjusted to pH 6.6 using HCl. A solution was obtained by this means which contains 5 mM Na$_2$EDTA.

The batch was left at room temperature in the dark until conversion was complete. The reaction was monitored by means of HPLC analysis. In this case, the starting material had disappeared after 70 hours.

The standard conditions of the analytical HPLC are:

Buffer A: 0.1 molar triethylammonium acetate buffer in water

Buffer B: 0.1 molar triethylammonium acetate buffer in water:acetonitrile 1:4

Gradient: starting from 10% B to 50% B in 40 minutes

Column material: 10 μM LiChrosphere® 100 RP-18 from Merck Darmstadt GmbH; 250×4

Retention time of the starting material: 18.8 minutes

Retention time of the product: several peaks from 13.9–36.2 minutes

After reaction was complete, the batch was diluted to four times the volume using water. A Waters Sep-Pak Cartridge RP-18 (from 15 OD 2 g of packing) was activated with 3×10 ml of acetonitrile and 3×10 ml of water, the oligo was applied and allowed to sink in, the reaction vessel was rewashed with 2×10 ml of water, and the cartridge was rewashed with 3×10 ml of water in order to remove salt and excess peptide, and eluted with 1:1 water: acetonitrile until no more product eluted by UV spectroscopy. The fractions were concentrated in the cold and in the dark, combined, and concentrated again.

The invention claim is:

1. A conjugate comprising a 4',2'-pentopyranosylnucleic acid covalently bonded through a linker to a biomolecule selected from the group consisting of a peptide, protein, nucleic acid, antibody, functional antibody moiety, DNA, and RNA, wherein the biomolecule does not non-covalently bond or hybridize to the pentopyranosylnucleic acid.

2. The conjugate according to claim 1, wherein the biomolecule is a peptide, protein or a nucleic acid.

3. The conjugate according to claim 1, wherein the biomolecule is an antibody, a functional moiety of an antibody, a DNA, or an RNA.

* * * * *